(12) United States Patent
Finley et al.

(10) Patent No.: US 9,201,073 B2
(45) Date of Patent: Dec. 1, 2015

(54) METHODS AND COMPOSITIONS FOR ENHANCING PROTEASOME ACTIVITY

(71) Applicant: President and Fellows of Harvard College, Cambridge, MA (US)

(72) Inventors: Daniel J. Finley, Jamaica Plain, MA (US); John W. Hanna, Boston, MA (US); Nathaniel A. Hathaway, San Francisco, CA (US); Randall W. King, Brookline, MA (US); Byung-Hoon Lee, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/022,337

(22) Filed: Sep. 10, 2013

(65) Prior Publication Data
US 2014/0199706 A1    Jul. 17, 2014

Related U.S. Application Data

(63) Continuation of application No. 12/601,551, filed as application No. PCT/US2008/006621 on May 23, 2008, now abandoned.

(60) Provisional application No. 60/931,745, filed on May 24, 2007.

(51) Int. Cl.
*G01N 33/573*    (2006.01)
*A61K 31/00*    (2006.01)
*C12Q 1/37*    (2006.01)

(52) U.S. Cl.
CPC .............. *G01N 33/573* (2013.01); *A61K 31/00* (2013.01); *C12Q 1/37* (2013.01); *G01N 2500/02* (2013.01)

(58) Field of Classification Search
CPC ..................................................... A61K 31/00
USPC ......................................................... 435/7.4
See application file for complete search history.

(56) References Cited

U.S. PATENT DOCUMENTS

| | | |
|---|---|---|
| 5,821,051 A | 10/1998 | Androphy et al. |
| 2001/0032339 A1 | 10/2001 | Zoghbi et al. |
| 2003/0082207 A1 | 5/2003 | Andre et al. |
| 2004/0138153 A1 | 7/2004 | Ramesh et al. |
| 2005/0112118 A1 | 5/2005 | Cimbora et al. |
| 2005/0203063 A1 | 9/2005 | Deshaies et al. |
| 2005/0267037 A1 | 12/2005 | Anderson et al. |
| 2005/0277762 A1 | 12/2005 | Ploegh et al. |
| 2006/0089321 A1 | 4/2006 | Walter et al. |
| 2006/0172295 A1 | 8/2006 | Bilbe et al. |
| 2006/0200870 A1 | 9/2006 | Tseng |

FOREIGN PATENT DOCUMENTS

WO    WO2007/041568 A2 *   4/2007   ............... C12N 9/48

OTHER PUBLICATIONS

Hu et al. "Structure and mechanisms of the proteasome-associated deubiquitinating enzyme USO14", EMBO, 2005, 24:3747-3756.*
Terpe "Overview of tag protein fusions: from molecular and biochemical fundamentals to commercial systems", Appl Microbiol Biotechnol., 2003, 60:523-533.*
Borodovsky et al. "A novel active site-directed probe specific for debiquitylating enzymes reveals proteasome association of USP14", EMBO, 2001,20(18):5187-5196.*
Borodovsky et al. The EMBO J, 2001, 20(18):5187-5196.*

* cited by examiner

*Primary Examiner* — Bin Shen
(74) *Attorney, Agent, or Firm* — Foley Hoag LLP

(57) ABSTRACT

This invention relates to methods and compositions for enhancing proteasome activity in a cell. The methods and compositions for enhancing the activity of the proteasome in cells modulate the activity of Ubp6 (yeast) or Usp14 (human), an endogenous inhibitor of the proteasome. The methods and compositions partially or completely reduce the inhibitory activity of Usp14 on a proteasome, thereby specifically enhancing the protein-degradation activity of the proteasome. The invention also provides methods of screening to identify inhibitors of Ubp6, Usp14, and/or both Ubp6 and Usp14.

9 Claims, 15 Drawing Sheets

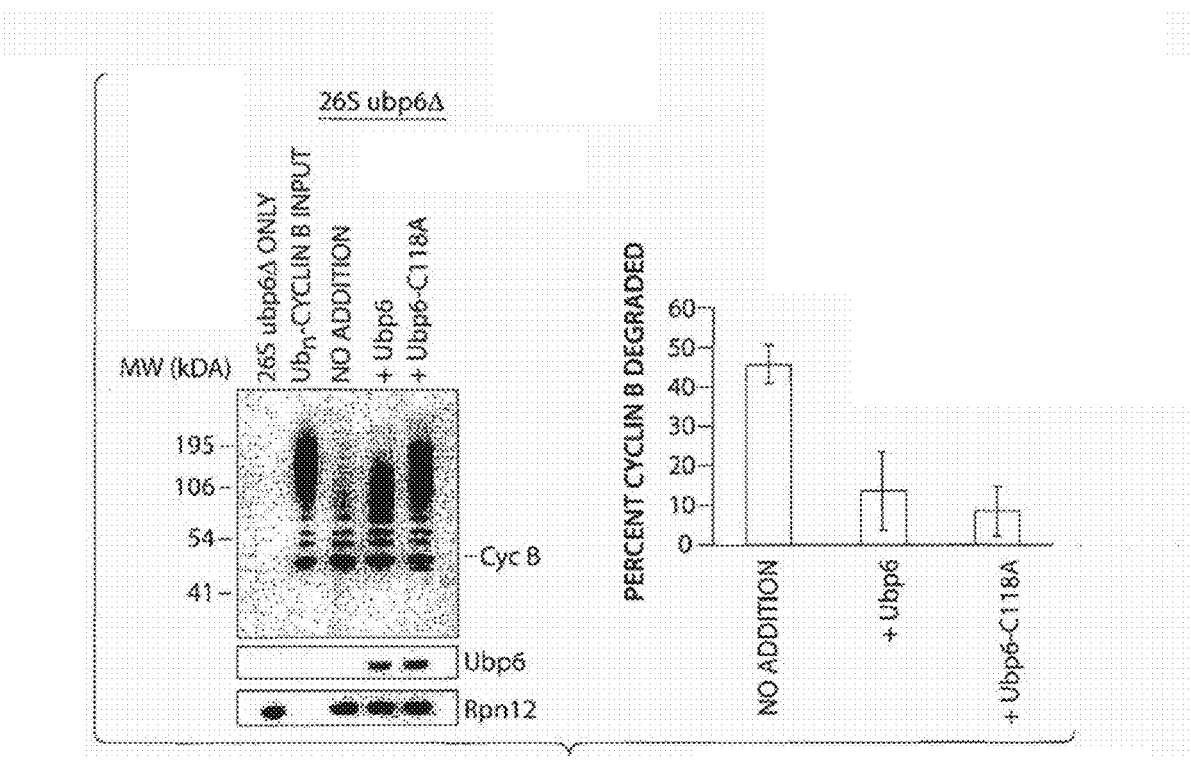
Fig. 4C
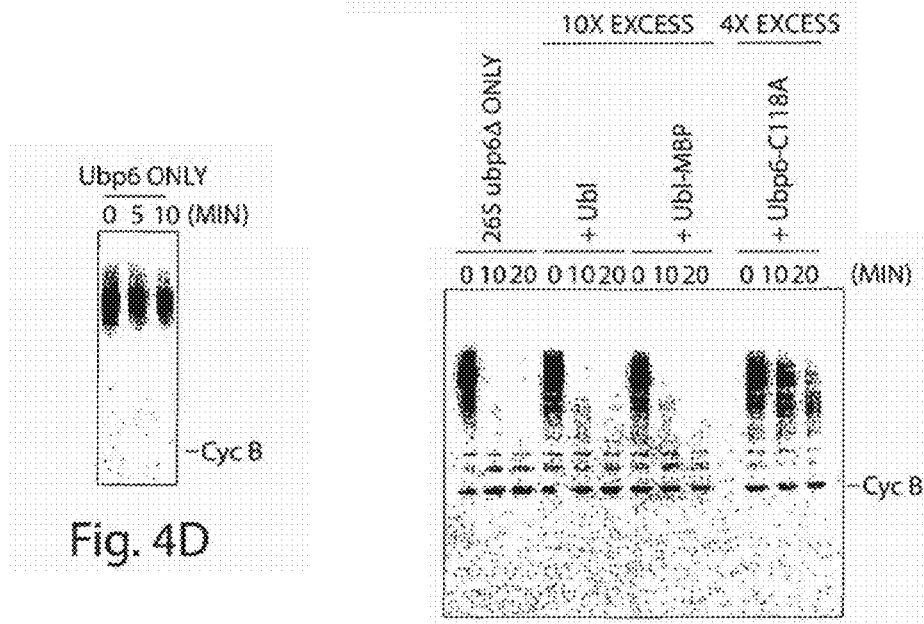
Fig. 4D
Fig. 4E

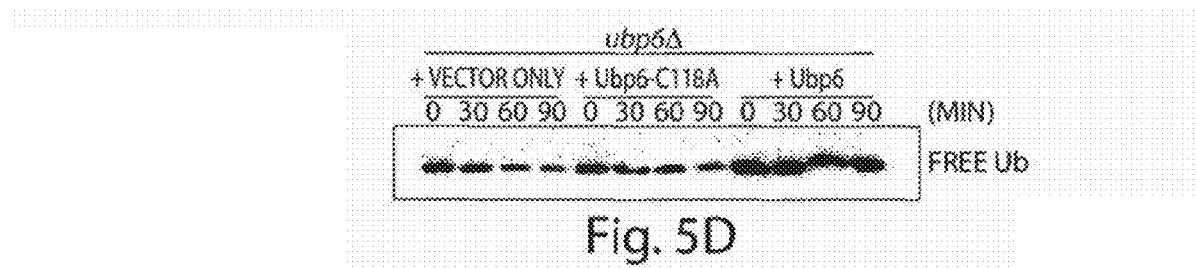
Fig. 5D
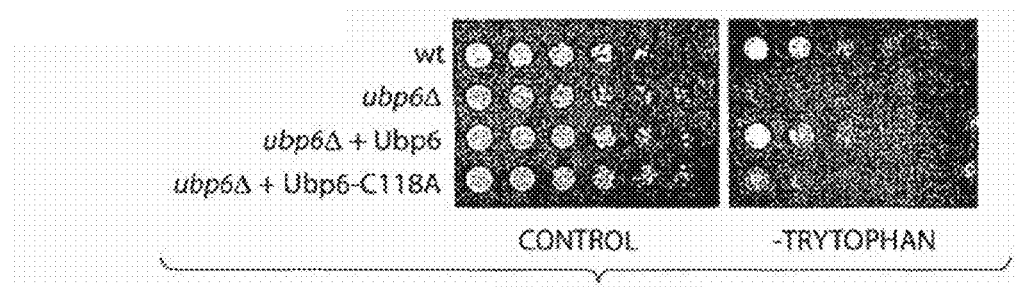
Fig. 5E
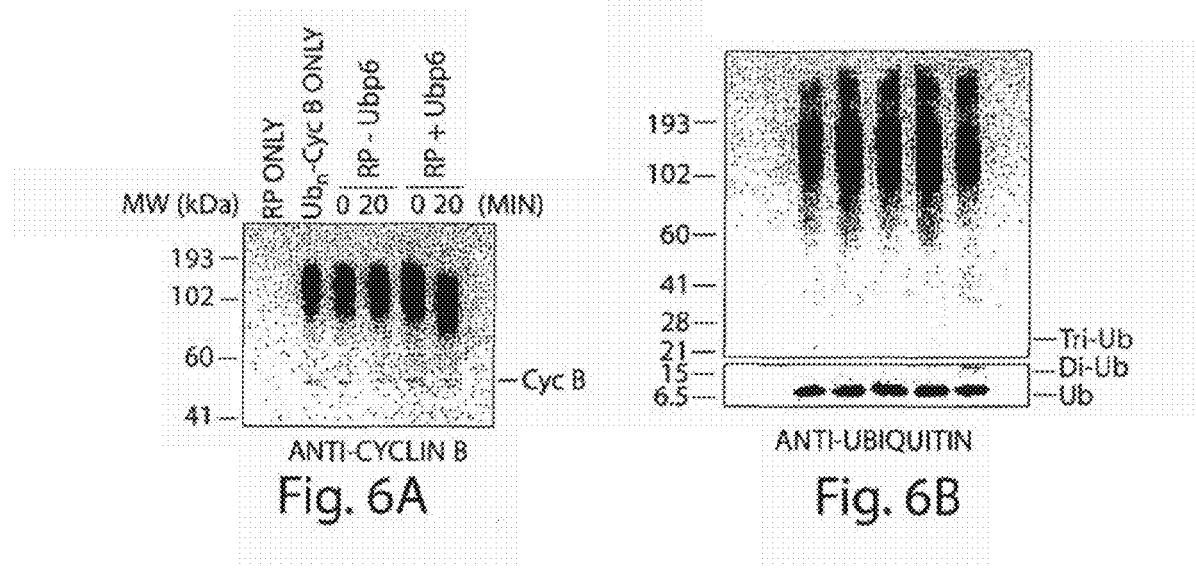
Fig. 6A
Fig. 6B

```
                          SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 1

Leu Leu Val Tyr
1

<210> SEQ ID NO 2
<211> LENGTH: 396
<212> TYPE: PRT
<213> ORGANISM: Homo sapiens

<400> SEQUENCE: 2

Ser Ala Met Glu Leu Pro Cys Gly Leu Thr Asn Leu Gly Asn Thr Cys
1               5                   10                  15

Tyr Met Asn Ala Thr Val Gln Cys Ile Arg Ser Val Pro Glu Leu Lys
            20                  25                  30

Asp Ala Leu Lys Arg Tyr Ala Gly Ala Leu Arg Ala Ser Gly Glu Met
        35                  40                  45

Ala Ser Ala Gln Tyr Ile Thr Ala Ala Leu Arg Asp Leu Phe Asp Ser
    50                  55                  60

Met Asp Lys Thr Ser Ser Ser Ile Pro Pro Ile Ile Leu Leu Gln Phe
65                  70                  75                  80

Leu His Met Ala Phe Pro Gln Phe Ala Glu Lys Gly Glu Gln Gly Gln
                85                  90                  95

Tyr Leu Gln Gln Asp Ala Asn Glu Cys Trp Ile Gln Met Met Arg Val
            100                 105                 110

Leu Gln Gln Lys Leu Glu Ala Ile Glu Asp Asp Ser Val Lys Glu Thr
        115                 120                 125

Asp Ser Ser Ser Ala Ser Ala Ala Thr Pro Ser Lys Lys Lys Ser Leu
    130                 135                 140

Ile Asp Gln Phe Phe Gly Val Glu Phe Glu Thr Thr Met Lys Cys Thr
145                 150                 155                 160

Glu Ser Glu Glu Glu Glu Val Thr Lys Gly Lys Glu Asn Gln Leu Gln
                165                 170                 175

Leu Ser Cys Phe Ile Asn Gln Glu Val Lys Tyr Leu Phe Thr Gly Leu
            180                 185                 190

Lys Leu Arg Leu Gln Glu Ile Thr Lys Gln Ser Pro Thr Leu Gln
        195                 200                 205

Arg Asn Ala Leu Tyr Ile Lys Ser Ser Lys Ile Ser Arg Leu Pro Ala
    210                 215                 220

Tyr Leu Thr Ile Gln Met Val Arg Phe Phe Tyr Lys Glu Lys Glu Ser
225                 230                 235                 240

Val Asn Ala Lys Val Leu Lys Asp Val Lys Phe Pro Leu Met Leu Asp
                245                 250                 255

Met Tyr Glu Leu Cys Thr Pro Glu Leu Gln Glu Lys Met Val Ser Phe
            260                 265                 270
```

```
Arg Ser Lys Phe Lys Asp Leu Glu Asp Lys Val Asn Gln Gln Pro
            275                 280                 285

Asn Thr Ser Asp Lys Lys Ser Ser Pro Gln Lys Glu Val Lys Tyr Glu
290                 295                 300

Pro Phe Ser Phe Ala Asp Asp Ile Gly Ser Asn Asn Cys Gly Tyr Tyr
305                 310                 315                 320

Asp Leu Gln Ala Val Leu Thr His Gln Gly Arg Ser Ser Ser Gly
            325                 330                 335

His Tyr Val Ser Trp Val Lys Arg Lys Gln Asp Glu Trp Ile Lys Phe
            340                 345                 350

Asp Asp Asp Lys Val Ser Ile Val Thr Pro Glu Asp Ile Leu Arg Leu
            355                 360                 365

Ser Gly Gly Gly Asp Trp His Ile Ala Tyr Val Leu Leu Tyr Gly Pro
370                 375                 380

Arg Arg Val Glu Ile Met Glu Glu Ser Glu Gln
385                 390                 395
```

<210> SEQ ID NO 3
<211> LENGTH: 397
<212> TYPE: PRT
<213> ORGANISM: Saccharomyces cerevisiae

<400> SEQUENCE: 3

```
Gln Phe Ala Gln Leu Pro Val Gly Phe Lys Asn Met Gly Asn Thr Cys
1               5                   10                  15

Tyr Leu Asn Ala Thr Leu Gln Ala Leu Tyr Arg Val Asn Asp Leu Arg
            20                  25                  30

Asp Met Ile Leu Asn Tyr Asn Pro Ser Gln Gly Val Ser Asn Ser Gly
            35                  40                  45

Ala Gln Asp Glu Glu Ile His Lys Gln Ile Val Ile Glu Met Lys Arg
50                  55                  60

Cys Phe Glu Asn Leu Gln Asn Lys Ser Phe Lys Ser Val Leu Pro Ile
65                  70                  75                  80

Val Leu Leu Asn Thr Leu Arg Lys Cys Tyr Pro Gln Phe Ala Glu Arg
            85                  90                  95

Asp Ser Gln Gly Gly Phe Tyr Lys Gln Gln Asp Ala Glu Glu Leu Phe
            100                 105                 110

Thr Gln Leu Phe His Ser Met Ser Ile Val Phe Gly Asp Lys Phe Ser
            115                 120                 125

Glu Asp Phe Arg Ile Gln Phe Lys Thr Thr Ile Lys Asp Thr Ala Asn
130                 135                 140

Asp Asn Asp Ile Thr Val Lys Glu Asn Glu Ser Asp Ser Lys Leu Gln
145                 150                 155                 160

Cys His Ile Ser Gly Thr Thr Asn Phe Met Arg Asn Gly Leu Leu Glu
            165                 170                 175

Gly Leu Asn Glu Lys Ile Glu Lys Arg Ser Asp Leu Thr Gly Ala Asn
            180                 185                 190

Ser Ile Tyr Ser Val Glu Lys Lys Ile Ser Arg Leu Pro Lys Phe Leu
            195                 200                 205

Thr Val Gln Tyr Val Arg Phe Phe Trp Lys Arg Ser Thr Asn Lys Lys
            210                 215                 220

Ser Lys Ile Leu Arg Lys Val Val Phe Pro Phe Gln Leu Asp Val Ala
225                 230                 235                 240

Asp Met Leu Thr Pro Glu Tyr Ala Ala Glu Lys Val Lys Val Arg Asp
```

```
                        245                 250                 255
Glu Leu Arg Lys Val Glu Lys Glu Lys Asn Glu Lys Glu Arg Glu Ile
            260                 265                 270

Lys Arg Arg Lys Phe Asp Pro Ser Ser Glu Asn Val Met Thr Pro
        275                 280                 285

Arg Glu Gln Tyr Glu Thr Gln Val Ala Leu Asn Glu Ser Glu Lys Asp
        290                 295                 300

Gln Trp Leu Glu Glu Tyr Lys Lys His Phe Pro Pro Asn Leu Glu Lys
305                 310                 315                 320

Gly Glu Asn Pro Ser Cys Val Tyr Asn Leu Ile Gly Val Ile Thr His
                325                 330                 335

Gln Gly Ala Asn Ser Glu Ser Gly His Tyr Gln Ala Phe Ile Arg Asp
            340                 345                 350

Glu Leu Asp Glu Asn Lys Trp Tyr Lys Phe Asn Asp Asp Lys Val Ser
                355                 360                 365

Val Val Glu Lys Glu Lys Ile Glu Ser Leu Ala Gly Gly Gly Glu Ser
        370                 375                 380

Asp Ser Ala Leu Ile Leu Met Tyr Lys Gly Phe Gly Leu
385                 390                 395

<210> SEQ ID NO 4
<211> LENGTH: 353
<212> TYPE: PRT
<213> ORGANISM: Homo sapiens

<400> SEQUENCE: 4

Lys Lys His Thr Gly Tyr Val Gly Leu Lys Asn Gln Gly Ala Thr Cys
1               5                   10                  15

Tyr Met Asn Ser Leu Leu Gln Thr Leu Phe Phe Thr Asn Gln Leu Arg
            20                  25                  30

Lys Ala Val Tyr Met Met Pro Thr Glu Gly Asp Asp Ser Ser Lys Ser
        35                  40                  45

Val Pro Leu Ala Leu Gln Arg Val Phe Tyr Glu Leu Gln His Ser Asp
    50                  55                  60

Lys Pro Val Gly Thr Lys Lys Leu Thr Lys Ser Phe Gly Trp Glu Thr
65                  70                  75                  80

Leu Asp Ser Phe Met Gln His Asp Val Gln Glu Leu Cys Arg Val Leu
                85                  90                  95

Leu Asp Asn Val Glu Asn Lys Met Lys Gly Thr Cys Val Glu Gly Thr
            100                 105                 110

Ile Pro Lys Leu Phe Arg Gly Lys Met Val Ser Tyr Ile Gln Cys Lys
        115                 120                 125

Glu Val Asp Tyr Arg Ser Asp Arg Arg Glu Asp Tyr Tyr Asp Ile Gln
    130                 135                 140

Leu Ser Ile Lys Gly Lys Lys Asn Ile Phe Glu Ser Phe Val Asp Tyr
145                 150                 155                 160

Val Ala Val Glu Gln Leu Asp Gly Asp Asn Lys Tyr Asp Ala Gly Glu
                165                 170                 175

His Gly Leu Gln Glu Ala Glu Lys Gly Val Lys Phe Leu Thr Leu Pro
            180                 185                 190

Pro Val Leu His Leu Gln Leu Met Arg Phe Met Tyr Asp Pro Gln Thr
        195                 200                 205

Asp Gln Asn Ile Lys Ile Asn Asp Arg Phe Glu Phe Pro Glu Gln Leu
    210                 215                 220
```

```
Pro Leu Asp Glu Phe Leu Gln Lys Thr Asp Pro Lys Asp Pro Ala Asn
225                 230                 235                 240

Tyr Ile Leu His Ala Val Leu Val His Ser Gly Asp Asn His Gly Gly
                245                 250                 255

His Tyr Val Val Tyr Leu Asn Pro Lys Gly Asp Gly Lys Trp Cys Lys
                260                 265                 270

Phe Asp Asp Asp Val Val Ser Arg Cys Thr Lys Glu Glu Ala Ile Glu
        275                 280                 285

His Asn Tyr Gly Gly His Asp Asp Leu Ser Val Arg His Cys Thr
    290                 295                 300

Asn Ala Tyr Met Leu Val Tyr Ile Arg Glu Ser Lys Leu Ser Glu Val
305                 310                 315                 320

Leu Gln Ala Val Thr Asp His Asp Ile Pro Gln Gln Leu Val Glu Arg
                325                 330                 335

Leu Gln Glu Glu Lys Arg Ile Glu Ala Gln Lys Arg Lys Glu Arg Gln
                340                 345                 350

Glu
```

METHODS AND COMPOSITIONS FOR ENHANCING PROTEASOME ACTIVITY

RELATED APPLICATION

This non-provisional patent application is a continuation of U.S. application Ser. No. 12/601,551, filed on Jun. 25, 2010, which is a national stage application, filed under 35 U.S.C. §371, of International Application No. PCT/US2008/006621, filed on May 23, 2008, which claims the benefit of U.S. Provisional Patent Application Ser. No. 60/931,745, filed May 24, 2007, the contents of which are herein incorporated by reference in their entirety.

STATEMENT AS TO FEDERALLY SPONSORED RESEARCH

This invention was made with U.S. Government support under National Institutes of Health Grant Nos. GM065592 and GM066492. The government has certain rights in the invention.

TECHNICAL FIELD

This invention relates to methods and compositions for enhancing proteasome activity in a cell.

BACKGROUND OF THE INVENTION

The ubiquitin-proteasome system is the major pathway for intracellular protein degradation in eukaryotes. Substrates of this pathway acquire a covalently linked polyubiquitin chain through the action of a cascade of ubiquitin activating and conjugating enzymes. This ubiquitin chain serves as the recognition motif for a large multi-subunit protease known as the proteasome, which processively degrades the substrate into small polypeptides while releasing ubiquitin for reuse (Pickart and Cohen. (2004). Proteasomes and their kin: proteases in the machine age. Nat. Rev. Mol. Cell. Biol. 5, 177-187).

SUMMARY OF THE INVENTION

The present invention provides methods and compositions for enhancing the activity of the proteasome in cells. When a ubiquitinated protein is degraded, the metabolic fates of ubiquitin and its conjugative target are uncoupled at the proteasome by deubiquitination. Proteasomes of budding yeast contain two deubiquitinating enzymes, Ubp6 and Rpn11. Rpn11 promotes protein breakdown through its degradation-coupled activity. In contrast, Ubp6 has a potent and evolutionarily conserved capacity to inhibit the proteasome in vitro and in vivo. However, inhibitory capacity is retained in a catalytically inactive point mutant of Ubp6, indicating that Ubp6 has both deubiquitinating activity and proteasome inhibitor activity. These functions cooperate in that inhibition of degradation by Ubp6 is accompanied by progressive trimming of the substrate's ubiquitin chain. Rpn11 catalyzes substrate-proximal chain cleavage, and Ubp6 inhibits degradation at or upstream of this step, so that inhibition of degradation by Ubp6 results in a switch in the mode of ubiquitin chain processing. Thus, Ubp6 regulates both the nature and magnitude of proteasome activity.

The methods and compositions for enhancing the activity of the proteasome in cells modulate the activity of a major component of the proteasome, known as Ubp6 (yeast) or Usp14 (human), an endogenous inhibitor of the proteasome. For example, the methods and compositions described herein reduce, e.g., partially or completely, the inhibitory activity of Usp14 on a proteasome, thereby specifically enhancing the protein-degradation activity of the proteasome. The invention also provides methods of screening to identify inhibitors of Ubp6, Usp14, and/or both Ubp6 and Usp14.

Usp14 is a deubiquitinating enzyme that binds tightly to the proteasome. The full-length human Usp14 contains 494 amino acids, with a 9 kDa Ubl domain (ubiquitin-like domain) at the N-terminus followed by a 45 kDa catalytic domain. (See Hu, et al. (2005). Structure and mechanisms of the proteasome-associated deubiquitinating enzyme Usp14. EMBO J. 24, 3747-3756). The Usp14 catalytic domain comprises residues 91-494 of the amino acid sequence shown, for example, in GenBank Accession No. P54578, hereby incorporated by reference in its entirety.

Understanding of this Usp14 protein has been achieved mainly through study of its yeast ortholog, Ubp6. Most proteasomes in the cell are complexed to Ubp6. Ubp6 is a strong inhibitor of proteasome function, both in vivo and in vitro. Thus, the proteasome, and the ubiquitin-proteasome pathway as a whole, operate in a partially inhibited state. This is an evolutionarily conserved property, because it has been found that Usp14 also has the capacity to inhibit yeast proteasomes.

As described herein, Ubp6 exerts a two-fold inhibitory influence on the proteasome: it inhibits proteasomes both catalytically and non-catalytically. Catalytic inhibition is mediated by the removal of ubiquitin groups from the ubiquitinated substrate protein. This is inhibitory because ubiquitin targets the substrate protein to the proteasome and is necessary for substrate degradation. Noncatalytic inhibition is defined as the component of proteasome inhibition observed when inhibition is accomplished using an active-site mutant of Ubp6.

The invention also provides methods of treating a proteinopathy (or protein-folding disease), including, by way of non-limiting example, neurodegenerative disorders and other diseases such as certain cancers. The methods of treating a proteinopathy include methods of reducing the severity of a proteinopathy, methods of reducing at least one symptom of a proteinopathy, and methods of stabilizing at least one symptom associated with a proteinopathy. The proteinopathy, or a symptom thereof, is, e.g., partially or completely alleviated using the methods described herein.

A major insight into human disease arising from studies of the last decade and more is that they are frequently caused by abnormal or misfolded proteins. These diseases are known collectively as proteinopathies and appear to be caused by the accumulation of aberrant proteins. Proteinopathies include, for example, many neurodegenerative diseases, such as, e.g., Alzheimer's Disease, Parkinson's Disease, Lewy Body Dementia, ALS, Huntington's Disease, Spinocerebellar Ataxias, and Spinobulbar Muscular Atrophy, and other diseases, including some cancers. In general, misfolded proteins are eliminated from the body by the proteasome. But in the case of such diseases, the proteasome cannot eliminate all of these harmful proteins. Thus, the methods of the present invention allow for the treatment or prevention of a proteinopathy by enhancing the activity of a proteasome through the administration of an inhibitor of Ubp6/Usp14. The enhanced activity of the proteasome, in turn, is used to remove the harmful proteins, thereby ameliorating such diseases. Currently, there is no recognized strategy for enhancing the activity of the proteasome pathway. As described herein, the proteasome pathway does not ordinarily operate at full efficiency, but rather it operates below its true capacity because the pathway is partially inhibited by Ubp6/Usp14. Thus, the inhibition of Ubp6/Usp14 of the methods and compositions described herein provide a simple approach to enhancing proteasome activity in the cell.

For example, it has been found that the absence of Ubp6 alleviated the effects of toxic, expanded forms of the Huntington gene product, when Huntington was expressed in yeast (FIG. 13). This phenomenon was independent of any effect of Ubp6 on ubiquitin levels, suggesting that the non-catalytic inhibitory effect of Ubp6 is most likely responsible.

The methods and compositions described herein are administered to a subject suffering from, or suspected of suffering from, a proteinopathy. A subject suffering from a proteinopathy is identified by methods known in the art. For example, a subject is suffering from a proteinopathy such as a neurological disorder is identified using any of a variety of clinical and/or laboratory tests such as, physical examination, radiologic examination and blood and/or urine analysis.

Administration of a Usp14 inhibitor to a patient suffering from, predisposed to, or suspected of suffering from, a proteinopathy is considered successful if any of a variety of laboratory or clinical results is achieved. For example, administration of a Usp14 inhibitor to a patient suffering from a proteinopathy is considered successful one or more of the symptoms associated with the disorder is alleviated, reduced, inhibited or does not progress to a further, i.e., worse, state. Administration of a Usp14 inhibitor to a patient suffering from a proteinopathy is considered successful if the disorder, e.g., a neurological disorder or certain cancers, enters remission or does not progress to a further, i.e., worse, state.

The invention described herein provides a method of enhancing proteasome activity in a cell by contacting, treating or otherwise exposing the cell with a Usp14 inhibitor in an amount sufficient to reduce endogenous inhibition of proteasome-mediated protein degradation. For example, the Usp14 inhibitor is a small-molecule inhibitor. A "small molecule", as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. For example, the Usp14 inhibitor interacts with, e.g., binds to or otherwise interferes with, at least a portion of the catalytic region of Usp14, e.g., residues 91-49 of the amino acid sequence shown in GenBank Accession No. P54578. In some embodiments, the Usp14 inhibitor interacts with, e.g., binds to or otherwise interferes with the binding surface, i.e., surface groove, between the Palm and Thumb region of Usp14. (Hu, et al. (2005). Structure and mechanisms of the proteasome-associated deubiquitinating enzyme Usp14. EMBO J. 24, 3747-3756). In some embodiments, the Usp14 inhibitor interacts with, e.g., binds to or otherwise interferes with a portion of the Usp14 polypeptide sequence of GenBank Accession No. P54578 selected from α1 helix (residues 114-124), α2 helix (residues 127-133), α3 helix (residues 147-165), α4 helix (residues 173-182), α5 helix (residues 200-214), α6 helix (residues 244-247), α7 helix (residues 287-291), α8 helix (residues 361-376), α9 helix (residues 460-464), β1 strand (residues 169-171), β2 strand (residues 249-251), β3 strand (residues 252-257), β4 strand (residues 269-271), β5 strand (residues 273-275), β6 strand (residues 296-301), β7 strand (residues 308-316), β8 strand (residues 325-329), β9 strand (residues 352-354), β10 strand (residues 418-428), β11 strand (residues 434-441), β12 strand (residues 447-449), β13 strand (residues 477-480), BL1 loop (residues 329-351), BL2 loop (residues 429-433), and any combinations thereof.

In some embodiments, the Usp14 inhibitor used in the methods of enhancing proteasome activity impedes, e.g., partially or completely, a catalytic activity of Usp14. For example, the Usp14 inhibitor interacts with the catalytic site of Usp14. In some embodiments of the methods of enhancing proteasome activity described herein, the Usp14 inhibitor impedes, e.g., partially or completely, a non-catalytic inhibitory activity of Usp14. For example, the Usp14 inhibitor increases the rate of proteasome-mediated degradation of ubiquitin or a ubiquitinated polypeptide as compared to the rate of proteasome-mediated degradation in the absence of the Usp14 inhibitor.

The invention also provides a method of treating a proteinopathy in a subject, or alleviating a symptom associated with a proteinopathy in a subject, by administering to the subject a Usp14 inhibitor in an amount effective to reduce inhibition of proteasome-mediated protein degradation by Usp14. As used herein, the term patient includes human and veterinary subjects. The term subject includes humans and other mammals. Proteinopathies to be treated by the methods described herein include, by way of non-limiting example, a neurodegenerative disorder or a cancer. For example, the proteinopathy is Huntington's disease. Alleviation of a symptom associated with a proteinopathy is, e.g., complete or partial.

In some embodiments, the Usp14 inhibitor is a small-molecule inhibitor. For example, the Usp14 inhibitor interacts with, e.g., binds to or otherwise interferes with, at least a portion of the catalytic region of Usp14, e.g., residues 91-49 of the amino acid sequence shown in GenBank Accession No. P54578. In some embodiments, the Usp14 inhibitor interacts with, e.g., binds to or otherwise interferes with the binding surface, i.e., surface groove, between the Palm and Thumb region of Usp14. (Hu, et al. (2005). Structure and mechanisms of the proteasome-associated deubiquitinating enzyme Usp14. EMBO J. 24, 3747-3756). In some embodiments, the Usp14 inhibitor interacts with, e.g., binds to or otherwise interferes with a portion of the Usp14 polypeptide sequence of GenBank Accession No. P54578 selected from α1 helix (residues 114-124), α2 helix (residues 127-133), α3 helix (residues 147-165), α4 helix (residues 173-182), α5 helix (residues 200-214), α6 helix (residues 244-247), α7 helix (residues 287-291), α8 helix (residues 361-376), α9 helix (residues 460-464), β1 strand (residues 169-171), β2 strand (residues 249-251), β3 strand (residues 252-257), β4 strand (residues 269-271), β5 strand (residues 273-275), β6 strand (residues 296-301), β7 strand (residues 308-316), β8 strand (residues 325-329), β9 strand (residues 352-354), β10 strand (residues 418-428), β11 strand (residues 434-441), β12 strand (residues 447-449), β13 strand (residues 477-480), BL1 loop (residues 329-351), BL2 loop (residues 429-433), and any combinations thereof.

In some embodiments of the methods of treating a proteinopathy described herein, the Usp14 inhibitor impedes, e.g., partially or completely, a catalytic activity of Usp14. For example, the Usp14 inhibitor interacts with the catalytic site of Usp14. In some embodiments, the Usp14 inhibitor used in the methods of treating a proteinopathy impedes, e.g., partially or completely, a non-catalytic inhibitory activity of Usp14. For example, the Usp14 inhibitor increases the rate of proteasome-mediated degradation of ubiquitin or a ubiquitinated polypeptide as compared to the rate of proteasome-mediated degradation in the absence of the Usp14 inhibitor.

The invention also provides a variety of screening assays useful to identify Usp14 inhibitors. For example, the invention described herein provides a method of screening for a Usp14 inhibitor by (i) providing a Usp14 polypeptide and a proteasome under conditions sufficient to allow the Usp14 polypeptide and proteasome to form a complex; (ii) contacting, treating or otherwise exposing the Usp14 polypeptide/proteasome complex with a test compound; and (iii) determining whether the test compound dissociates the Usp14 polypeptide/proteasome complex, whereby dissociation of the Usp14 polypeptide/proteasome complex indicates that the test compound is a Usp14 inhibitor. The test compound is, for example, a small molecule, and the proteasome is selected from a yeast proteasome, a murine proteasome and a human proteasome. The test compound is optionally detectably labeled.

In some embodiments of the methods of screening for a Usp14 inhibitor, the Usp14 inhibitor to be identified impedes, e.g., partially or completely, a catalytic activity of Usp14. For example, the Usp14 inhibitor interacts with the catalytic site of Usp14. In some embodiments, the Usp14 inhibitor used in this screening method impedes, e.g., partially or completely, a non-catalytic inhibitory activity of Usp14. For example, the Usp14 inhibitor increases the rate of proteasome-mediated degradation of ubiquitin or a ubiquitinated polypeptide as compared to the rate of proteasome-mediated degradation in the absence of the Usp14 inhibitor.

The invention also provides a method of screening for a Usp14 inhibitor that interacts with the catalytic site of Usp14 by (i) providing a test solution comprising Usp14 polypeptide and a proteasome under conditions sufficient to allow the Usp14 polypeptide and proteasome to form a complex; (ii) contacting, treating or otherwise exposing the test solution with a test compound and a substrate of the Usp14 polypeptide/proteasome, wherein the substrate is coupled to a reporter that is detectable after cleavage by a deubiquitinating enzyme; (iii) determining whether the substrate is deubiquitinated in the presence of the test compound and the Usp14 polypeptide/proteasome complex, whereby an absence of deubiquitination of the substrate in the presence of the test compound and the Usp14 polypeptide/proteasome complex indicates that the test compound interacts with the Usp14 catalytic site. In some embodiments, the substrate is ubiquitin-AMC. The test compound is, for example, a small molecule. In some embodiments, the reporter is fluorescently labeled.

The invention also provides a method of screening for Usp14 inhibitors that impede, e.g., partially or completely, non-catalytic proteasome inhibition by Usp14 by (i) providing a test solution comprising Usp14 polypeptide and a proteasome under conditions sufficient to allow the Usp14 polypeptide and proteasome to form a complex; (ii) contacting, treating or otherwise exposing the test solution with a test compound and a ubiquitinated cyclin B polypeptide; (iii) determining the rate of degradation of the ubiquitinated cyclin B polypeptide in the presence of the test compound; and (iv) comparing the rate of degradation of the ubiquitinated cyclin B polypeptide in the absence of the test compound; whereby an increased rate of degradation of ubiquitinated cyclin B in the presence of the test compound as compared to the rate of degradation in the absence of the test compound indicates that the test compound is an inhibitor of non-catalytic proteasome inhibition by Usp14. The Usp14 polypeptide is, for example, a catalytically inactivated form of Usp14. For example, the Usp14 polypeptide contains a mutation, e.g., amino acid substitution, deletion, and/or insertion, at one or more residues in the catalytic domain, e.g., residues 91-49 of the amino acid sequence shown in GenBank Accession No. P54578. For example, one or more catalytically active residues is mutated, such as for example, Cys114, His435 and Asp451 residues of the amino acid sequence shown in GenBank Accession No. P54578. In some embodiments, the test compound is a small molecule. The proteasome is, for example, selected from a yeast proteasome, a murine proteasome and a human proteasome. In some embodiments, the ubiquitinated cyclin B polypeptide is a ubiquitinated form of a cyclin B-luciferase fusion protein.

Other features, objects, and advantages of the invention will be apparent from the description and drawings. All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same.

BRIEF DESCRIPTION OF THE DRAWINGS

FIGS. 1A, 1B and 1C depict the processing of ub-cyclin B in vitro by wild-type or ubp6Δ proteasomes, visualized by immunoblot with antibodies to cyclin B1 (FIG. 1A), Ubp6 (FIG. 1B), or proteasome subunit Rpn5 (FIG. 1C).

FIG. 1D compares wild-type and ubp6Δ proteasomes (10 μg), as determined by SDS-PAGE followed by Coomassie staining.

FIG. 1E is a graph depicting proteasome-dependent hydrolysis of suc-LLVY-AMC (SEQ ID NO: 1), a ubiquitin-independent fluorogenic proteasome substrate. Error bars reflect standard deviations.

FIG. 2A depicts the effect of purified Ubp6 on proteasome-mediated ub-cyclin B processing in the presence or absence of epoxomicin (100 μM).

FIGS. 2B and 2C depicts processing of ub-cyclin B by wild-type and ubp6Δ proteasomes in the presence or absence of epoxomicin. Ub-cyclin B was synthesized with wild-type or K48R ubiquitin, as indicated.

FIG. 3A depicts the growth of wild-type (SYT303), ubp6Δ (SJH170), and ubr1Δ (SYT304) yeast strains on media containing or lacking tryptophan, as indicated.

FIG. 3B depicts cycloheximide-chase reactions examining turnover of the Ura3 and Trp 1 reporter proteins in wild-type (SYT318), ubp6Δ (SJH126), and ubr1Δ (SYT342) strains. Reactions were visualized with immunoblots using antibodies against the HA-epitope or proteasome subunit, Rpn5, as indicated. The far right represents shorter exposure of the ubr1Δ lanes.

FIGS. 4A-4F are a series of illustrations and graphs depicting a non-catalytic function of Ubp6 in proteasome inhibition.

FIG. 4A is a schematic representation of the various Ubp6 mutants, MBP, maltose-binding protein.

FIGS. 4B and 4E depict Ub-cyclin B processing by ubp6Δ proteasomes, in the presence or absence of the indicated Ubp6 species.

FIG. 4C includes an illustration and a graph depicting a comparison of the extent of proteasome inhibition by wild-type Ubp6 and Ubp6-C118A by quantitative mass spectrometry. The upper panels of FIG. 4C depict immunoblots using anti-cyclin B, -Ubp6, and -Rpn12 antibodies as indicated. The lower panel of FIG. 4C depicts quantitation results. Error bars represent the standard deviation of two independent quantitations.

FIG. 4D depicts the failure of Ubp6 to deubiquitinate cyclin B when proteasomes are absent.

FIG. 4F depicts the electrophoretic mobility shift of proteasome bound to ubiquitinated Cdc34. Proteasomes were visualized using the fluorogenic substrate suc-LLVY-AMC (SEQ ID NO: 1).

FIGS. 5A-5E are a series of illustrations depicting in vivo differentiation of ubp6Δ and ubp6-C118A mutants.

FIGS. 5A and 5B depict the growth of wild-type (SJH30), wild-type overexpressing ubiquitin (SJH34), ubp6Δ (SJH31), and ubp6Δ overexpressing ubiquitin (SJH35) yeast stains on selective plates containing copper sulfate (100 μM) in the presence or absence of canavanine (1.5 μg/ml) or rapamycin (200 ng/ml), and grown at 30° C. for 3-7 days.

FIG. 5C depicts the growth of wild-type (SJH152), ubp6Δ (SJH153), ubp6Δ expressing wild-type Ubp6 (SJH154), and ubp6Δ expressing Ubp6-C118A (SJH155) yeast strains on selective plates containing no drug, canavanine (1.5 μg/ml), or rapamycin (200 ng/ml) as indicated, and grown at 30° C. for 3-7 days. For SJH154 and SJH155, duplicates represent two independent transformants.

FIG. 5D depicts cycloheximide-chase analyses of free ubiquitin turnover conducted in wild-type (SJH120), ubp6Δ overexpressing wild-type Ubp6 (SJH20), and ubp6Δ overexpressing Ubp6-C118A (SJH22) strains, as indicated.

FIG. 5E depicts the growth of wild-type (SJH171), ubp6Δ (SJH172), ubp6Δ expressing wild-type Ubp6 (SJH173), and ubp6Δ expressing Ubp6-C118A (SJH174) yeast strains on selective media containing or lacking tryptophan, as indicated.

FIGS. 6A-6C are a series of illustrations depicting degradation independence and evolutionary conservation of Ubp6 function.

FIGS. 6A and 6B depict the processing of ub-cyclin B by RP (ubp6Δ) in the presence or absence of purified Ubp6. Reactions were visualized by immunoblotting with anti-cyclin B antibody or anti-ubiquitin antibody, as indicated.

FIG. 6C depicts the effect of Ubp6 or its human homolog, Usp14, on the processing of ub-cyclin B by yeast ubp6Δ proteasomes.

FIG. 9A depicts the result of an in vitro ub-cyclin B assay carried out with ubp6Δ proteasomes (135 nM) supplemented with wild-type Ubp6 (540 nM) and ubiquitinvinyl sulfone (2.5 μM), as indicated. The lower panel is anti-Ubp6 immunoblot showing modification of Ubp6 by Ub-VS. Ubp6 was present in four-fold molar excess over proteasome, and thus only a fraction of Ubp6 protein was modified.

FIG. 9B depicts the results of Ub-AMC (0.5 μM) hydroylsis assay.

DETAILED DESCRIPTION

Figure 1A:
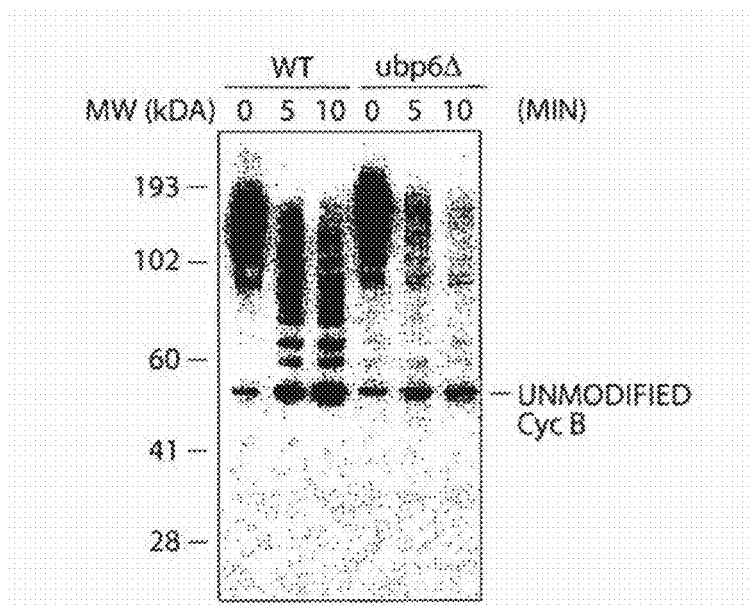
FIGS. 1A-1E are a series of illustrations and graphs depicting the ability of Upb6 to inhibit degradation of ubiquitinated cyclin B by purified yeast proteasomes.
Figure 1B:

The ubiquitin-proteasome system is the major pathway for intracellular protein degradation in eukaryotes. Substrates of this pathway acquire a covalently linked polyubiquitin chain through the action of a cascade of ubiquitin activating and conjugating enzymes. This ubiquitin chain serves as the recognition motif for a large multi-subunit protease known as the proteasome, which processively degrades the substrate into small polypeptides while releasing ubiquitin for reuse (Pickart and Cohen. (2004). Proteasomes and their kin: proteases in the machine age. Nat. Rev. Mol. Cell. Biol. 5, 177-187).

The proteasome is an approximately 2.5-MDa protein complex consisting of at least 33 distinct subunits in yeast (Pickart and Cohen, 2004). Its proteolytic active sites are housed at the center of the structure in a barrel-shaped subcomplex known as the core particle (CP, or 20S complex) (Groll, et al. (1997). Structure of 20S proteasome from yeast at 2.4 A resolution. Nature 386, 463-471). At either axial end of the CP, a second subcomplex known as the regulatory particle (RP, or 19S complex or PA 700) may bind. When one or both ends of the CP are occupied by the RP, the structure is referred to as the 26S proteasome. The RP comprises two subcomplexes of its own: the base and the lid (Glickman, et al. (1998). A subcomplex of the proteasome regulatory particle required for ubiquitin-conjugate degradation and related to the COP9-signalosome and eIF3. Cell 94, 615-623). The base is proximal to the CP and contains, among other proteins, six ATPases that are thought to form a ring structure that abuts the CP. The lid is distal to the CP and its subunit Rpn11 is thought to possess a metalloprotease-based deubiquitinating activity (Verma, et al. (2002). Role of Rpn11 metalloprotease in deubiquitination and degradation by the 26S proteasome. Science 298, 611-615; Yao and Cohen. (2002). A cryptic protease couples deubiquitination and degradation by the proteasome. Nature 419, 403-407; Maytal-Kivity, et al. (2002). MPN+, a putative catalytic motif found in a subset of MPN domain proteins from eukaryotes and prokaryotes, is critical for Rpn 11 function. BMC Biochem. 3, 28).

The proteasome displays a number of characteristics unusual for a protease. First, its proteolytic active sites are sequestered within the hollow cylindrical chamber of the CP (Groll, et al. (1997). Structure of 20S proteasome from yeast at 2.4 A resolution. Nature 386, 463-471). Providing access to this internal chamber are narrow gates at either end of the CP, and gating appears to be modulated by the Rpt2 subunit of the base (Pickart and Cohen. (2004). Proteasomes and their kin: proteases in the machine age. Nat. Rev. Mol. Cell. Biol. 5, 177-187). These features presumably serve to prevent the unregulated destruction of intracellular proteins, and also impose a requirement for substrate unfolding, as most folded proteins are too large to pass through the open translocation channel leading to the CP. Protein unfolding is apparently mediated by the six ATPases of the base (Braun, et al. (1999). The base of the proteasome regulatory particle exhibits chaperone-like activity. Nat. Cell Biol. 1, 221-226), which may explain, at least in part, a second unusual feature of the proteasome, its ATP dependence. Finally, substrate recognition by the proteasome is, with some exceptions, dependent on the presence of a ubiquitin chain. Multiple ubiquitin receptors have been identified, some of which are core proteasomal subunits while others are substoichiometric proteasome-associating factors (Elsasser and Finley. (2005). Delivery of ubiquitinated substrates to protein-unfolding machines. Nat Cell Biol. 7, 742-9). At some point after recognition, the ubiquitin chain is removed from the substrate to facilitate substrate degradation and to minimize degradation of ubiquitin. This function is carried out by deubiquitinating enzymes that reside in the proteasome.

In budding yeast S. cerevisiae, at least two deubiquitinating enzymes are thought to contribute to deubiquitination by the proteasome: Rpn11 and Ubp6 (Leggett, et al. (2002). Multiple associated proteins regulate proteasome structure and function. Mol. Cell. 10, 495-507; Verma, et al. (2002). Role of Rpn11 metalloprotease in deubiquitination and degradation by the 26S proteasome. Science 298, 611-615; Yao and Cohen. (2002). A cryptic protease couples deubiquitination and degradation by the proteasome. Nature 419, 403-407; Maytal-Kivity, et al. (2002). MPN+, a putative catalytic motif found in a subset of MPN domain proteins from eukaryotes and prokaryotes, is critical for Rpn11 function. BMC Biochem. 3, 28; Chemova, et al. (2003). Pleiotropic effects of Ubp6 loss on drug sensitivities and yeast prion are due to depletion of the free ubiquitin pool. J. Biol. Chem. 278, 52102-52115; Guterman and Glickman. (2004). Complementary roles for Rpn11 and Ubp6 in deubiquitination and proteolysis by the proteasome. J. Biol. Chem. 279, 1729-1738). Rpn11 is a core structural component of the lid, and whereas most deubiquitinating enzymes utilize a cysteine-based proteolytic mechanism, Rpn11 is thought to be a metalloprotease. Point mutations in its metal-coordinating site impair substrate degradation in vitro and vivo, indicating a positive role for Rpn11 in protein degradation (Verma, et al. (2002). Role of Rpn11 metalloprotease in deubiquitination and degradation by the 26S proteasome. Science 298, 611-615; Yao and Cohen. (2002). A cryptic protease couples deubiquitination and degradation by the proteasome. Nature 419, 403-407).

The second proteasomal deubiquitinating enzyme, Ubp6, has been classified as a proteasome-associated protein, largely on the basis of its ready dissociation from the proteasome in the presence of high salt concentrations (Leggett, et al. (2002). Multiple associated proteins regulate proteasome structure and function. Mol. Cell. 10, 495-507). Ubp6, a cysteine protease, is an abundant component of proteasomes (Verma, et al. (2000). Proteasomal proteomics: identification of nucleotide-sensitive proteasome-interacting proteins by mass spectrometric analysis of affinity-purified proteasomes. Mol. Biol. Cell. 11, 3425-3439; Leggett et al., 2002), and in contrast to Rpn11, Ubp6 associates with the base. An N-terminal ubiquitin-like domain (Ubl) of Ubp6 mediates this interaction. Binding of Ubp6 to the proteasome activates Ubp6's catalytic activity over 300-fold (Leggett et al., 2002), indicating an intimate functional relationship between Ubp6 and the proteasome. However, the precise role of Ubp6 in proteasome function has remained uncertain. Some reports have assigned Ubp6 little or no role in proteasome-mediated deubiquitination or degradation, while others have argued that Ubp6, like Rpn11, facilitates proteasome-mediated degradation.

The data and examples provided herein present the first detailed analysis of how Ubp6 affects the degradation of a physiological substrate of the proteasome. Ubp6 inhibits protein breakdown by the proteasome, that a major component of its inhibitory effect is non-catalyticin nature. The inhibitory effect was observed in vivo and in vitro, and on different test substrates. During the degradation delay that Ubp6 imposes, substrate deubiquitination proceeds on proteasomes, but the mode of deubiquitination is altered from that seen in the absence of Ubp6: degradation-linked "en bloc" chain removal by Rpn11 is replaced by progressive chain trimming by Ubp6. Thus, Ubp6 uses catalytic and noncatalytic mechanisms to modulate proteasome function, and the coordinated activity of multiple proteasomal deubiquitinating enzymes controls substrate fate.

Ubp6, a proteasomal deubiquitinating enzyme, is an endogenous proteasome inhibitor. Proteasomes regenerate ubiquitin by separating it from substrate prior to substrate degradation. However, it seems unlikely that this function alone could account for the existence of three distinct deubiquitinating enzymes in the proteasomes of most eukaryotes. Indeed, the mammalian proteasome has as many distinct active sites for deubiquitination as it has proteolytic active sites for substrate hydrolysis.

The activity of one proteasomal deubiquitinating enzyme, Rpn11, is coupled to and facilitates degradation (Verma, et al. (2002). Role of Rpn11 metalloprotease in deubiquitination and degradation by the 26S proteasome. Science 298, 611-615; Yao and Cohen. (2002). A cryptic protease couples deubiquitination and degradation by the proteasome. Nature 419, 403-407). The studies, data and examples provided herein demonstrate that another proteasomal deubiquitinating enzyme, Ubp6, has the capacity to inhibit degradation. Studies with Uch37 have shown that a proteasomal deubiquitinating enzyme can potentially antagonize degradation by premature deubiquitination (Lam, et al. (1997). Editing of ubiquitin conjugates by an isopeptidase in the 26S proteasome. Nature 385, 737-740).

However, Ubp6 antagonizes degradation by a novel mechanism that does not require deubiquitination of the degradative substrate: it inhibits the proteasome directly. Proteasomes operate on ub-cyclin B in vitro with substantially reduced efficiency when they are bound to Ubp6, and Ubp6 shows a comparable in vivo effect in reducing flux of at least some specific substrates through the proteasome. Thus, by virtue of Ubp6 the proteasome is under strong inhibitory control under standard growth conditions.

Substrate deubiquitination by Rpn11 is negatively controlled by Ubp6. One effect of Ubp6's inhibitory action is to prevent en bloc deubiquitination of the substrate by Rpn11 (FIG. 2). During the degradation delay imposed by Ubp6, its own deubiquitinating activity is operational, as can be seen in a gradual reduction in the number of substrate-bound ubiquitin groups (FIGS. 4 and 6). Thus, Ubp6 disassembles the ubiquitin chains and inhibits the degradation of the same substrate. In this way, the mode of substrate deubiquitination is significantly altered from that seen in the absence of Ubp6. These results show that the proteasome has distinct modes of deubiquitination, and that the en bloc mode is subject to negative control, principally by anon-catalytic function of Ubp6.

If Ubp6 were to inhibit degradation downstream of Rpn11, the substrate would lack ubiquitin modification during degradation delay. In this scenario, release from Ubp6-mediated inhibition is unproductive, as substrates lacking a ubiquitin modification dissociate from the proteasome rather than degrade. Thus, inhibition of the proteasome by Ubp6 delays the decision of whether the substrate will be degraded, and during the delay, attrition of the ubiquitin chain on the substrate proceeds gradually through the activity of Ubp6. The length of time allowed for delay of degradation is an important parameter. During this time period, shortening of the chain beyond a critical length leads to dissociation of the substrate from the proteasome. This model indicates the presence of two distinct activities in Ubp6, catalytic and non-catalytic in nature.

Figure 5A:
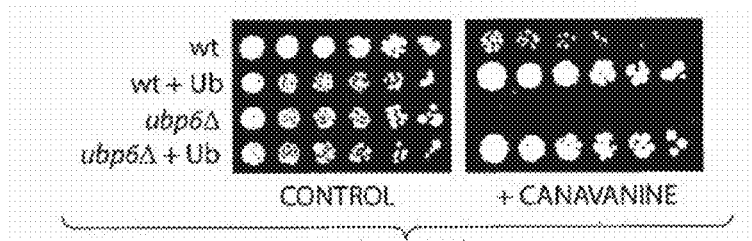

The catalytic activity of Ubp6 also inhibits degradation, and in a manner that is strongly dependent on the duration of non-catalytic inhibition. The in vivo data (FIG. 5E) provide support for this mechanism. However, the extent of cyclin B ubiquitination achieved in the in vitro reaction may be high enough that limited chain attrition does not compromise binding of the conjugate to the proteasome, while substrates bearing shorter chains, or exposed to longer time courses, would display such an inhibitory capacity of Ubp6 more clearly.

The Mechanism of Proteasome Inhibition by Ubp6:

The studies provided herein in the Examples elucidate the mechanism of proteasome inhibition by Ubp6. These studies provide the first demonstration that a deubiquitinating enzyme utilize non-catalytic functions to modulate the activity of another protein or complex. No interference with substrate binding on the part of Ubp6 was observed, and an interaction between Ubp6 and the proteasome mediates inhibition. Ubp6 is tethered to the proteasome through its Ubl domain, which binds subunit Rpn1 of the base (Leggett, et al. (2002). Multiple associated proteins regulate proteasome structure and function. Mol. Cell. 10, 495-5072002; Stone, et al. (2004). Uch2/Uch37 is the major deubiquitinating enzyme associated with the 26S proteasome in fission yeast. J. Mol. Biol. 344, 697-706). However, proteasome binding by the Ubl domain itself has no inhibitory effect (FIG. 4E). Indeed, both the Ubl and C-terminal domains are required for inhibition. A simple model is that the Ubl domain serves only a proteasome-tethering role and that the C-terminal domain contains the specific sequence information for inhibition. Crystal structures of Ubp6 and its mammalian homolog, USP14, indicate several regions within the C-terminal domain of Ubp6, including a notable surface-exposed alpha helix, that are not conserved with the unrelated deubiquitinating enzyme HAUSP, and are unlikely to contribute to enzymatic activity (Hu, et al. (2005). Structure and mechanisms of the proteasome-associated deubiquitinating enzyme USP14. EMBO J. 24, 3747-3756). In contrast, these regions are highly conserved among Ubp6 homologs, and it may be that one of these regions mediates the non-catalytic activity of the protein.

The studies presented herein in the Examples were designed to rule out roles for Ubp6 in substrate targeting (FIGS. 4E and F), gate opening (FIG. 1E), modulation of CP active sites (FIG. 1E), as well as modulation of overall proteasomal ATPase activity. Previous studies suggested that the C-terminal domain of Ubp6 has lid-binding activity (Leggett et al., 2002); this interaction might effect inhibition. This model is particularly interesting since the lid is required for full activation of Ubp6 upon complex formation with the proteasome (Leggett et al., 2002). Thus, the same Ubp6-lid binding event could conceivably inhibit the proteasome and assist in the activation of Ubp6. Since Rpn11 is a component of the lid, the lid interaction model also indicates that Ubp6 inhibits degradation by directly inhibiting Rpn11 rather than an unknown step upstream of Rpn11.

Proteasome inhibition by Ubp6 is not complete. Although this is not surprising (complete inhibition of the proteasome would be detrimental), the mechanism by which inhibition is relieved is unclear. It is also unclear whether release of the proteasome from Ubp6-mediated inhibition is itself a regulated step. Since Ubp6 is not an integral subunit of the proteasome, the fraction of proteasomes associated with Ubp6 can be freely varied. The extent of proteasome inhibition is optionally also regulated by altering cellular Ubp6 levels, or alternatively via post-translational modulation of Ubp6 activity.

Studies are also designed to determine the scope of proteasome inhibition by Ubp6, i.e., the generality of the degradation-inhibitory effect of Ubp6. To determine how substrate-specific the inhibitory effects of Ubp6 are, studies are designed to determine the effect of ubp6 mutations on the rates of degradation of a wider variety of substrates. If substrates are affected to very different degrees by Ubp6, it would suggest that Ubp6 may slow degradation rates to enhance the selectivity of protein degradation by the proteasome. Studies of nucleotide polymerases (Joyce and Benkovic. (2004).

DNA polymerase fidelity: kinetics, structure, and checkpoints. Biochemistry 43, 14317-14324) as well as protein synthesis (Cochella and Green. (2005). Fidelity in protein synthesis. Curr. Biol. 15, R536-540) have shown that that speed and fidelity cannot be optimized simultaneously, but are competing functional criteria. The definition of fidelity for a protease cannot be as clear as for a polymerase, but fidelity may be more easily defined from the standpoint of the fate of ubiquitin groups than of substrates. Ubp6 clearly enhances ubiquitin sparing by the proteasome both in vitro and in vivo, and thus enhances a significant aspect of its fidelity.

Several previous studies have reported Ubp6 to play positive roles in the degradation of specific proteins (Leggett, et al. (2002). Multiple associated proteins regulate proteasome structure and function. Mol. Cell. 10, 495-507; Miura and Abe. (2004). Multiple ubiquitin-specific protease genes are involved in degradation of yeast tryptophan permease Tat2 at high pressure. FEMS Microbiol. Lett. 239, 171-179), in contrast to the data and results presented in the Examples herein. These observations do not appear to reflect the scope of the proteasome-inhibitory effect described here, but rather the critical role of Ubp6 in maintaining cellular ubiquitin levels, and the importance of ubiquitin levels in determining the degradation rates of these particular proteins. For example, yeast Tat2 can be degraded in a UBP6-dependent manner, but Tat2 is a membrane protein and its degradation proceeds through the vacuole rather than the proteasome. In addition, Tat2 degradation is sensitive to mutations in other genes that affect cellular ubiquitin levels (Miura and Abe, 2004). The other known example is ubiquitin-proline 13-galactosidase (Leggett et al., 2002), whose degradation is highly sensitive to ubiquitin levels (Johnson, et al. (1995). A proteolytic pathway that recognizes ubiquitin as a degradation signal. J. Biol. Chem. 270, 17442-17456).

The substrate-stabilizing effects of ubiquitin deficiency could obscure the destabilizing effects of release from proteasome inhibition in the ubp6Δ mutant. Studies are designed to uncouple these opposing effects in ataxia mice, whose biochemical basis is loss-of-function mutation in Ubp6/Usp14. These mice display a severe neurologic phenotype culminating in widespread paralysis and premature death (Wilson, et al. (2002). Synaptic defects in ataxia mice result from a mutation in Usp14, encoding a ubiquitin-specific protease. Nat. Genet. 32, 420-425). Studies are designed to determine whether these phenotypes are a result of ubiquitin depletion or enhanced proteasomal degradation, or both, and whether either of these cellular phenomena have relevance for human neurologic or neurodegenerative diseases.

In recent years, pharmacologic inhibition of the proteasome's proteolytic active sites has emerged as an effective anti-cancer treatment in such clinical contexts as multiple myeloma (Adams, J. (2004). The development of proteasome inhibitors as anticancer drugs. Cancer Cell. 5, 417-421). The efficacy of such drugs may reflect an increased requirement for proteasome function in some cancer cells. On the other hand, a deficit of proteasome function can contribute significantly to pathophysiology. Deficient proteasome function has been suggested, for example, to underlie various proteinopathies and neurodegenerative diseases (Goldberg. (2003). Protein degradation and protection against misfolded or damaged proteins. Nature 426, 895-899). For diseases characterized by proteasome deficiency, drugs that inhibit a broadly acting proteasome inhibitor such as Ubp6 provide an effective therapy.

Structure and Function of Usp14:

The full-length human Usp14 contains 494 amino acids, with a 9 kDa Ubl domain (ubiquitin-like domain) at the N-terminus followed by a 45 kDa catalytic domain. (See Hu, et al. (2005). Structure and mechanisms of the proteasome-associated deubiquitinating enzyme Usp14. EMBO J. 24, 3747-3756, hereby incorporated by reference in its entirety). The Usp14 catalytic domain comprises residues 91-494 of the amino acid sequence shown, for example, in GenBank Accession No. P54578, hereby incorporated by reference in its entirety.

The family of ubiquitin-specific processing protease (UBP) are cysteine proteases that contain highly divergent sequences and exhibit strong homology mainly in two regions that surround the catalytic Cys and His residues; these are the so-called Cys Box (~19 amino acids) and the His Box (60-90 amino acids) (See e.g., Hu et al.; Papa FR, and Hochstrasser M (1993) The yeast DOA4 gene encodes a deubiquitinating enzyme related to a product of the human tre-2 oncogene. Nature 366: 313-319; D'Andrea A, and Pellman D (1998) Deubiquitinating enzymes: a new class of biological regulators. Crit Rev Biochem Mol Biol 33: 337-352).

The catalytic domain of Usp14 resembles an extended right hand comprised of three domains: Fingers, Palm, and Thumb (see e.g., Hu et al. at FIGS. 1 and 2). The three-domain organization creates a prominent binding surface between the Fingers and the Palm-Thumb scaffold, which is predicted to bind to ubiquitin. Usp14 binds to ubiquitin using the Fingers domain and the surface groove between the Palm and the Thumb. (Hu et al. 2005). The Ubl domain of Usp14 is responsible for binding to the 19S regulatory particle (RP) of the 26S proteasome.

In Usp14, the Thumb contains 6 α helices ($\alpha 1$-$\alpha 6$) and one short β strand ($\beta 1$), with the N-terminal Cys Box adopting an extended conformation. The Palm consists of a six-stranded $\beta 5$, $\beta 8$, $\beta 10$-$\beta 13$) central β sheet, three α helices ($\alpha 7$-$\alpha 9$), one short β strand ($\beta 9$), and several surface loops. Notably, two surface loops hover above and partially fill the predicted binding pocket for the C-terminus of ubiquitin. These two loops are named blocking loops 1 and 2 (BL1 and BL2). The Fingers comprise five β strands ($\beta 2$-$\beta 4$, $\beta 6$, and $\beta 7$). Packing interactions between the central β sheet in the Palm and the globular Thumb do not give rise to an interdomain cleft between the Palm and the Thumb, which is needed for the accommodation of ubiquitin C-terminus.

The Cys114, His435 and Asp451 residues of Usp14 form a catalytic triad in the active site of free (i.e., unbound) Usp14. Although the catalytic triad residues already adopt a productive conformation, access to these residues by ubiquitin is restricted. (Hu et al. 2005) Right above the active site of USP14, the two surface loops BL2 and BL1 are positioned very close to the predicted binding groove for the C-terminus of ubiquitin. Loops BL2 and BL1 would likely block access of the C-terminus of ubiquitin to the active site of USP14. Thus, the blockade of the ubiquitin C-terminus binding groove by loops BL2 and BL1 must be removed in order for USP14 to catalyze deubiquitination. Upon binding to ubiquitin, the active site of Usp14 undergoes conformational changes, for example at residues Tyr333, Phe 331 and Ser 432, which act in concert to accommodate the C-terminus of ubiquitin in the cleft between the Palm and Thumb domains formed by the conformational changes. (Hu et al. 2005). The conformational changes in the BL1 and BL2 loops are facilitated by interactions between conserved residues in these loops and residues on ubiquitin. (Ibid.).

Figure 15:
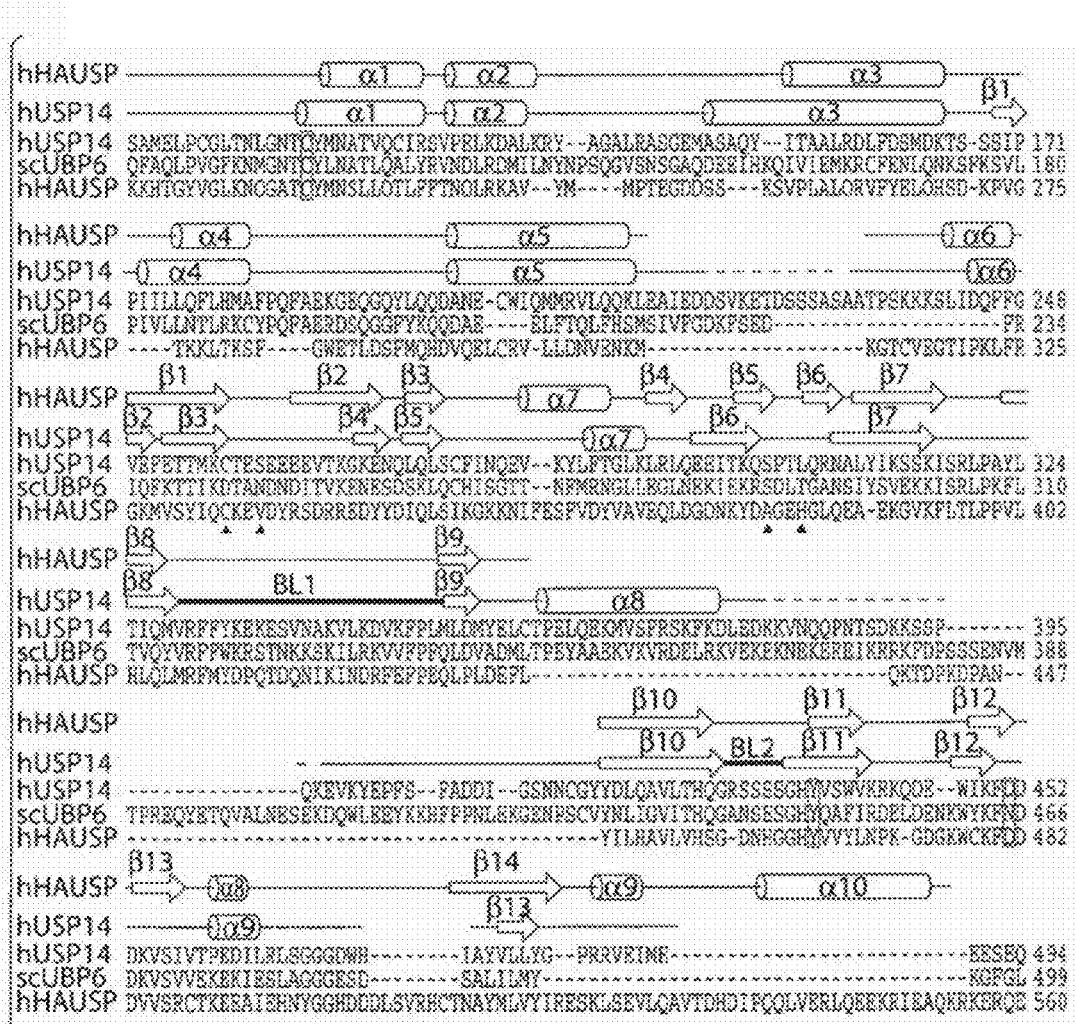
FIG. 15 is an illustration depicting a sequence alignment of Usp14, its yeast ortholog Ubp6 and another member of the UBP family, HAUSP (also known as Usp7) taken from Hu, et al. (2005). EMBO J. 24, 3747-3756. Conserved residues are shaded whereas the catalytic triad residues are highlighted by a vertical shaded box. The secondary structural elements above the sequences are indicated for free USP14 (lower) and HAUSP (upper). The four black arrowheads indicate the positions where Cys residues are supposed to be located in a zinc ribbon (Krishna S S, and Grishin N V (2004) The finger domain of the human deubiquitinating enzyme HAUSP is a zinc ribbon. Cell Cycle 3: 1046-1049). Sequence alignment employed the program ClustalW. Entries shown are from the SwissProt Database: HAUSP (SEQ ID NO: 4) (Human; W:Q93009); USP14 (SEQ ID NO: 2) (Human; SW:P54578); and UBP6 (SEQ ID NO: 3) (S. cerevisiae; SW:P35127).

As described above, Ubp6 is the functional homolog of Usp14 in *Saccharomyces cerevisiae* and shares 31% sequence identity with Usp14 in the catalytic core domain. A comparison of the sequences of Usp14 and Ubp6 is shown in FIG. 15, taken from Hu et al. (2005). It has been shown that the structure of the Usp14 catalytic domain is also very similar to that of the catalytic core domain from Ubp6 (see e.g., RCSB Protein Data Bank, Accession No. 1VJV). Similar to Usp14, Ubp6 contains two surface loops that are located above and partially block the predicted binding pocket for the C-terminus of ubiquitin (see e.g., FIG. 1C of Hu et al.). These two surface loops exhibit nearly identical topology as BL1 and BL2 in Usp14 (Ibid.). The local structural differences between Usp14 and Ubp6 concentrate in surface regions whereas the core structural elements are nearly identical to each other (Ibid.). The active site of Ubp6 adopts a highly similar conformation to that of Usp14 and includes the catalytic triad residues of Cys118, His447, and Asn465. (Hu et al. 2005).

The details of one or more embodiments of the invention are set forth in the accompanying description herein. Although any methods and materials similar or equivalent to those described herein can be used in the practice or testing of the present invention, the preferred methods and materials are now described. Other features, objects and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict; the present specification will control.

EXAMPLES

Example 1

Materials and Methods

Yeast Strains:
The yeast strains used herein are presented below in Table 1. Standard techniques were used for strain constructions and transformations. Yeast were cultured at 30° C. YPD medium consisted of 1% yeast extract, 2% Bacto-peptone, and 2% dextrose. Synthetic medium consisted of 0.7% Difco Yeast Nitrogen Base supplemented with amino acids, adenine, uracil, and 2% dextrose.

Recombinant Proteins:
The recombinant proteins used herein are presented below in Table 1. Recombinant proteins were expressed as GST-fusion proteins, purified by glutathione-Sepharose affinity chromatography, and eluted by thrombin cleavage, as described (Leggett, et al. (2002). Multiple associated proteins regulate proteasome structure and function. Mol. Cell. 10, 495-507). Eluates were treated with benzamidine or benzamidine-Sepharose to inactivate thrombin.

Ubp6-C118A mutants were generated by site-directed mutagenesis using the Quikchange System™ (Stratagene), and verified by DNA sequencing. The Ubl-MBP construct was generated by fusing the first 83 codons from UBP6 to the 5′-end of the complete coding sequence of the maltose binding protein from *E. coli*.

TABLE 1

Strains and Plasmids

| Strain | Genotype | Reference |
|---|---|---|
| SUB62 | MATa lys2-801 leu2-3, 2-112 ura3-52 his3-Δ200 trp1-1 | Finley et al., 1987* |
| MHY821 | MATa lys2-801 leu2-3, 2-112 ura3-52 his3-Δ200 trp1-1 ubp6::HIS3 | Amerik et al., 2000† |
| SY255C | MATa lys2-801 leu2-3, 2-112 ura3-52 his3-Δ200 trp1-1 ubp6::HIS3 | This study |
| SDL133 | MATa lys2-801 leu2-3, 2-112 ura3-52 his3-Δ200 trp1-1 rpn11::RPN11-TEVProA (HIS3) | Leggett et al., 2002 (same as SDL66) |
| SDL145 | MATa lys2-801 leu2-3, 2-112 ura3-52 his3-Δ200 trp1-1 rpn11::RPN11-TEVProA (HIS3) ubp6::URA3 | Leggett et al., 2002 |
| SYT234 | MATa lys2-801 leu2-3, 2-112 his3-Δ200 trp1-1 URA3 | This study |
| SYT235 | MATa lys2-801 leu2-3, 2-112 ura3-52 his3-Δ200 TRP1 | This study |
| SYT303 | MATa lys2-801 leu2-3, 2-112 ura3-52 his3-Δ200 trp1-1 $P_{CUP1}$-Ub-K-TRP1::NAT | This study |
| SYT304 | MATa lys2-801 leu2-3, 2-112 ura3-52 his3-Δ200 trp1-1 $P_{CUP1}$-Ub-K-TRP1::NAT ubr1Δ::LEU2 | This study |
| SJH138 | MATa lys2-801 leu2-3, 2-112 ura3-52 his3-Δ200 trp1-1 $P_{CUP1}$-Ub-K-TRP1::NAT ubp6::KAN | This study |
| SYT170 | MATa lys2-801 leu2-3, 2-112 ura3-52 his3-Δ200 trp1-1 $P_{CUP1}$-Ub-K-TRP1::NAT ubp6::HIS3 | This study |
| SYT295 | MATa lys2-801 leu2-3, 2-112 ura3-52 his3-Δ200 trp1-1 $P_{CUP1}$-U-K-URA3::NAT | This study |
| SYT293 | MATa lys2-801 leu2-3, 2-112 ura3-52 his3-Δ200 trp1-1 $P_{CUP1}$-U-K-URA3::NAT ubr1Δ::LEU2 | This study |
| SYT318 | MATa lys2-801 leu2-3, 2-112 ura3-52 his3-Δ200 trp1-1 $P_{CUP1}$-Ub-K-TRP1::NAT $P_{CUP1}$-Ub-K-URA3::NAT | This study |
| SYT342 | MATa lys2-801 leu2-3, 2-112 ura3-52 his3-Δ200 trp1-1 $P_{CUP1}$-Ub-K-TRP1::NAT $P_{CUP1}$-Ub-K-URA3::NAT ubr1Δ::KAN | This study |
| SJH126 | MATa lys2-801 leu2-3, 2-112 ura3-52 his3-Δ200 trp1-1 $P_{CUP1}$-Ub-K-TRP1::NAT $P_{CUP1}$-Ub-K URA3::NAT ubp6::KAN | This study |
| SJH30 | MATa lys2-801 leu2-3, 2-112 ura3-52 his3-Δ200 trp1-1 [YEp46Δ] | Hanna et al., 2003 |
| SJH34 | MATa lys2-801 leu2-3, 2-112 ura3-52 his3-Δ200 trp1-1[Yep96] | Hanna et al., 2003 |

TABLE 1-continued

Strains and Plasmids

| | | |
|---|---|---|
| SJH31 | MATa lys2-801 leu2-3, 2-112 ura3-52 his3-Δ200 trp1-1ubp6::URA3 [YEp46Δ] | Hanna et al., 2003 |
| SJH35 | MATa lys2-801 leu2-3, 2-112 ura3-52 his3-Δ200 trp1-1ubp6::URA3 [Yep96] | Hanna et al., 2003 |
| SJH152 | MATa lys2-801 leu2-3, 2-112 ura3-52 his3-Δ200 trp1-1 [YCplac22] | This study |
| SJH153 | MATa lys2-801 leu2-3, 2-112 ura3-52 his3-Δ200 trp1-1 ubp6::HIS3 [YCplac22] | This study |
| SJH154 | MATa lys2-801 leu2-3, 2-112 ura3-52 his3-Δ200 trp1-1 ubp6::HIS3 [pJH60] | This study |
| SJH155 | MATa lys2-8-01 leu2-3, 2-112 ura3-52 his3-Δ200 trp1-1 ubp6::HIS3 [pJH61] | This study |
| SJH120 | MATa lys2-801 leu2-3, 2-112 ura3-52 his3-Δ200 trp1-1 ubp6::URA3 [YEplac181] | This study |
| SJH20 | MATa lys2-801 leu2-3, 2-112 ura3-52 his3-Δ200 trp1-1 ubp6::URA3 [pJH3] | This study |
| SJH22 | MATa lys2-801 leu2-3, 2-112 ura3-52 his3-Δ200 trp1-1 ubp6::URA3 [pJH5] | This study |
| SJH171 | MATa lys2-801 leu2-3, 2-112 ura3-52 his3-Δ200 trp1-1 $P_{CUP1}$-Ub-K-TRP1::NAT[YCplac33] | This study |
| SJH172 | MATa lys2-801 leu2-3, 2-112 ura3-52 his3-Δ200 trp1-1 $P_{CUP1}$-Ub-K-TRP1::NAT ubp6::KAN[YCplac33] | This study |
| SJH173 | MATa lys2-801 leu2-3, 2-112 ura3-52 his3-Δ200 trp1-1 $P_{CUP1}$-Ub-K-TRP1::NAT ubp6::KAN[pJH80] | This study |
| SJH174 | MATa lys2-801 leu2-3, 2-112 ura3-52 his3-Δ200 trp1-1 $P_{CUP1}$-Ub-K-TRP1::NAT ubp6::KAN[pJH81] | This study |

| Plasmid | Details | Reference |
|---|---|---|
| pDL74 | GST-Ubp6 (pGEX4T-1) | Leggett et al., 2002 |
| pDL73 | GST-Ubp6-Ubl∆(pGEX-4T-1) | Leggett et al., 2002 |
| pJH1 | GST-Ubp6-C118A (pGEX-4T-1) | This study |
| pDL72 | GST-Ubl (pGEX-4T-1) | Leggett et al., 2002 |
| pJH56 | GST-Ubl-MBP (pGEX4T-1) | This study |
| | GST-Usp14 (pGEX-4T-1) | Hu et al., 2005 |
| pJH3 | Ubp6 (YEplac181[2μ/LEU2]) | This study |
| pJH5 | Ubp6-C118A (YEplac181 [2μ/LEU2]) | This study |
| pJH60 | Ubp6 (YCplac22 [CEN/TRP1]) | This study |
| pJH61 | Ubp6-C118A (YCplac22 [CEN/TRP1]) | This study |
| pJH80 | Ubp6 (YCplac33 [CEN/URA3]) | This study |
| pJH81 | Ubp6-C118A (YCplac33 [CEN/URA3]) | This study |

*Finley et al., (1987). The yeast polyubiquitin gene 1s essential for resistance to high temperatures, starvation, and other stresses. Cell 48, 1035-1046.
†Amerik, et al., (2000). Analysis of the deubiquitinating enzymes of the yeast Saccharomyces cerevisiae. Biol. Chem. 381, 981-992).

Proteasome Purification:

A previously described procedure for purification of the proteasome (Leggett, et al. (2002). Multiple associated proteins regulate proteasome structure and function. Mol. Cell. 10, 495-507) was modified by adding 1 mM ATP and 5 mM MgCl$_2$ to all purification buffers, and by washing resins with 100 bed vol. of buffer containing 50 mM NaCl, as opposed to 50 bed vol. of buffer containing 100 mM NaCl. RP was purified in the presence of ATP and MgCl$_2$ as described (Leggett et al., 2002).

In Vitro Deubiquitination/Degradation Assays:

Proteasomes (135 nM) were incubated with ub-cyclin B in the presence of 1 mM ATP and buffer (50 mM Tris [pH 7.51, 1 mM EDTA, 5 mM MgCl$_2$) for the indicated times. Reactions were terminated by the addition of 5×SDS Laemmli loading buffer (Leggett, et al. (2002). Multiple associated proteins regulate proteasome structure and function. Mol. Cell. 10, 495-507) and boiled for 5 min. Where indicated, recombinant, purified Ubp6 or Usp14 species (540 nM) were preincubated with proteasomes for 5 min prior to the reaction. Ubl and Ubl-MBP species were used at 1.35 μM to compensate for lower affinity of these species for proteasome binding compared to full length Ubp6 species (Leggett et al., 2002). Epoxomicin (100 μM) was used to inhibit proteolytic activity of proteasomes. Unless otherwise noted, immunoblots were visualized with anti-cyclin B1 polyclonal antibodies. Polyclonal antibodies recognizing Ubp6, Rpn5, Rpn12, and ubiquitin were used as indicated. Ub-cyclin B was added in molar excess over proteasome, generally on the order of 25-fold, except for FIGS. 4C, 6A and 6B, where the substrate:enzyme ratio was increased by a factor of five.

Figure 6C:
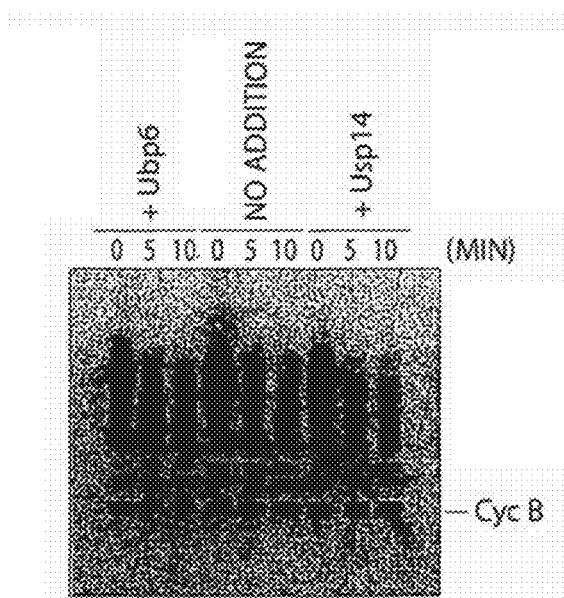

In the experiments of FIGS. 1, 4 (except FIG. 4C), and 6C, time points were sampled after the preparation of a single reaction mixture. The zero time points therefore reflect a lag which represents the amount of time required to sample the first time point after having prepared the reaction mixture. This time lag was consistent between samples, and less than 20 seconds. However, the activity of Ubp6 is rapid enough to reduce cyclin B ubiquitination by time zero. In the experiments of FIGS. 2, 4C, and 6 (except 6C), each time point was carried out as an independent reaction. The zero time points were prepared in the presence of 5×LLB, and accordingly, no processing could occur before time zero.

In Vivo Degradation Assays:

For plating assays, three-fold serial dilutions of yeast cultures grown in YPD were spotted onto plates containing or lacking tryptophan. For cycloheximide chase assays, exponential cultures in YPD supplemented with 100 μM copper sulfate (to further induce expression of the reporter proteins) were normalized to an equivalent cell density and cycloheximide (50 μg/mL) was added. At the indicated time points, an aliquot of each culture was removed, and cells were pelleted and resuspended in 1×LLB. Samples were immediately frozen on dry ice for the remainder of the time course, and subsequently boiled for 5 min. Visualization was by immunoblotting with anti-HA antibody (12CA5) or anti-Rpn5 antibody, as indicated.

Ubiquitination of Cyclin B:

Ubiquitination of cyclin B was carried out. Briefly, for each 30 μl reaction, Anaphase Promoting Complex (APC) was immunopurified from 600 μl of mitotic *Xenopus* egg extract with 12 μg of anti-Cdc27 antibodies (AF3.1, Santa Cruz Biotechnologies, Santa Cruz, Calif.) bound to 30 μl of Affiprep Protein A beads (Bio-Rad, Hercules, Calif.). Beads were washed three times with XB high salt (10 mM potassium HEPES pH 7.7, 500 mM KCl, 0.1 mM $CaCl_2$, 1 mM $MgCl_2$), two times with XB (same but with 100 mM KCl), and then three times into the reaction buffer (20 mM Tris pH 7.5, 100 mM KCl, 2.5 mM $MgCl_2$, 2 mM ATP). Ubiquitination reactions contained immunoprecipitated APC on 30 μl of beads, and 30 μl of a mix containing recombinant MBP-human E1 at 200 μg/ml, histidine-tagged Ubc4 at 66 μg/ml, ubiquitin at 1.25 mg/ml, and 50 μg/ml of histidine-tagged cyclin B1/cdc2 complex expressed in baculovirus. Reactions were incubated for 90 minutes at 22° C. with agitation on a shaker at 1,000 RPM. Reaction supernatants were combined with the eluate from the wash of beads with 20 μl of reaction buffer. Reactions were either used fresh after preparation or frozen at −80° C. until use with purified proteasomes.

Construction of N-End Rule Reporter Proteins:

The CUP1 promoter and the ubiquitin-Lys-LacI extension were amplified from the plasmid pUb166 by polymerase chain reaction (PCR) using the primers YT146 and YT147. The resulting fragment was digested with the restriction endonucleases SphI and HindIII and inserted into pUC119 to generate pYT602. A 2×-HA epitope was constructed using synthetic oligonucleotides bearing HindIII and XhoI restriction sites, and inserted by blunt-end ligation into the SmaI site of pUC119 to generate pYT598. The PstI/HindIII fragment from pYT602 and the HindIII/XhoI fragment from pYT598 were inserted into pBluescript-KS to yield pYT614. A ClonNAT cassette from pAG25 (Goldstein and McCusker. (1999). Three new dominant drug resistance cassettes for gene disruption in *Saccharomyces cerevisiae*. Yeast 15, 154 1-53) was then inserted N-terminally at the NotI site yielding pYT616. This plasmid contains the sequence ClonNAT[P-Cup1]-Ub-K-LacI-2×HA.

For the TRP1 fusion construct, a 100-base pair (bp) region from 5'-untranslated region of the gene immediately adjacent to the open reading frame start site was amplified from YDp-W (Berben, et al. (1991). The YDp plasmids: a uniform set of vectors bearing versatile gene disruption cassettes for *Saccharomyces cerevisiae*. Yeast 7, 475-7) by PCR using the primers YT169 and YT180; a 520 bp region from the 5' end of the TRP1 coding region was amplified from the plasmid YDp-W using YT164 and YT165. Utilizing PCR with the primers YT169 and YT165, these two fragments were co-amplified with the ClonNAT-[P-Cup1]-Ub-K-LacI-2×HA fragment, positioning the 5'-untranslated region of TRP1 at the 5' end of the fragment, and the TRP1 ORF region immediately downstream of and in frame with the HA epitope. The URA3 fusion construct was assembled analogously, using the primers YT158 and YT179 (for the 5' untranslated region of URA3) and YT160 and YT161 (for the ORF of the URA3 gene), and YDp-U (Berben, et al. (1991). The YDp plasmids: a uniform set of vectors bearing versatile gene disruption cassettes for *Saccharomyces cerevisiae*. Yeast 7, 475-7) as the source of the URA3 DNA.

Strains sYT234 and sYT235 were constructed by transforming SUB62 with wildtype DNA from URA3 and TRP1, respectively, and selecting for colonies that were either TRP+ or URA+. Strains bearing the Trp1 or Ura3 reporter proteins were generated by homologous recombination at the endogenous locus by transformation with the appropriate PCR fragment. Positive transformants were verified by PCR.

Quantitation of Proteasome Inhibition:

A standard substrate degradation assay was carried out, and analyzed in parallel by SDS-PAGE followed by Coomassie blue staining and immunoblot with anti-cyclin B antibody. Immunoblots were used to identify and excise the cyclin B-containing regions of the Coomassie-stained gel, and the lanes were analyzed by mass spectrometry.

Ub-Cdc34 Binding Assay:

Binding of ubiquitinated-Cdc34 (8 pmoles) to proteasome (4 pmoles) was carried by native gel electrophoresis followed by overlay of the fluorogenic activity-based probe, suc-LLVY-AMC (SEQ ID NO: 1), as previously described (Elsasser, et al. (2004). Rad23 and Rpn10 serve as alternative ubiquitin receptors for the proteasome. J. Biol. Chem. 279, 26817-26822). Ubp6 or Ubp6-C118A (8 pmoles) were preincubated with proteasomes prior to substrate addition.

In Vivo Assays of Drug Sensitivity:

Cultures were grown in synthetic media lacking tryptophan, normalized to an $OD_{600}$ of 0.2, spotted in three-fold serial dilutions onto plates consisting of synthetic media supplemented with the appropriate drug as indicated, and incubated at 30° C. for 3-7 days. For ubiquitin overexpression, plates were supplemented with copper sulfate (100 μM) to augment plasmid expression.

Analysis of In Vivo Ubiquitin Turnover:

Exponential phase cultures of the indicated strains bearing GAL-inducible UBP6 genes were grown in selective media containing 2% raffinose and 2% galactose. Cultures were normalized by $OD_{600}$ and cycloheximide was added to a final concentration of 50 μg/ml. Ubiquitin depletion in the presence of Ubp6 is minimized at this drug concentration, but increases at higher levels of cycloheximide (Hanna, et al. (2003). Ubiquitin depletion as a key mediator of toxicity by translational inhibitors. Mol. Cell. Biol. 23, 9251-9261). Aliquots were taken at the indicated time points after cycloheximide addition and $OD_{600}$ was measured to ensure that an equal number of cells was taken at each time point. Aliquots were processed and analyzed as previously described (Hanna et al., 2003).

Recombinant Usp14:

Recombinant GST-Usp14 was expressed in *E. coli* Rosetta cells (Novagen) and purified by glutathione-Sepharose affinity resins. The GST moiety was removed prior to the degradation assay, using the protease thrombin.

Human Proteasome:

A stable 293 cell line expressing hRpn11-HTBH was used. Human proteasomes were purified as previously described with some modifications (Wang X and Huang L (2007) Identifying dynamic interactors of protein complexes by quantitative mass spectrometry. Mol Cell Proteomics. 2008 January; 7(1):46-57. Epub 2007 Oct. 12.

In Vitro Ubn-Cyclin B1 Degradation Assay:

Assays were performed in proteasome preparation buffer (50 mM Tris [pH 7.5], 5 mM $MgCl_2$, and 5 mM ATP) at ambient temperature for the indicated times. The 26S human proteasomes (4 nM) were incubated with approximately 30 nM of Ub-conjugated cyclin B1 as substrates. Cyclin was ubiquitinated using purified APC ubiquitin ligase. Where indicated, a 15-fold molar access of recombinant Usp14 over proteasomes were preincubated prior to adding Ubn-cyclin B1.

Example 2

Ubp6 Inhibition of the Degradation of Ubiquitinated Cyclin B

Figure 1C:
Figure 1D:
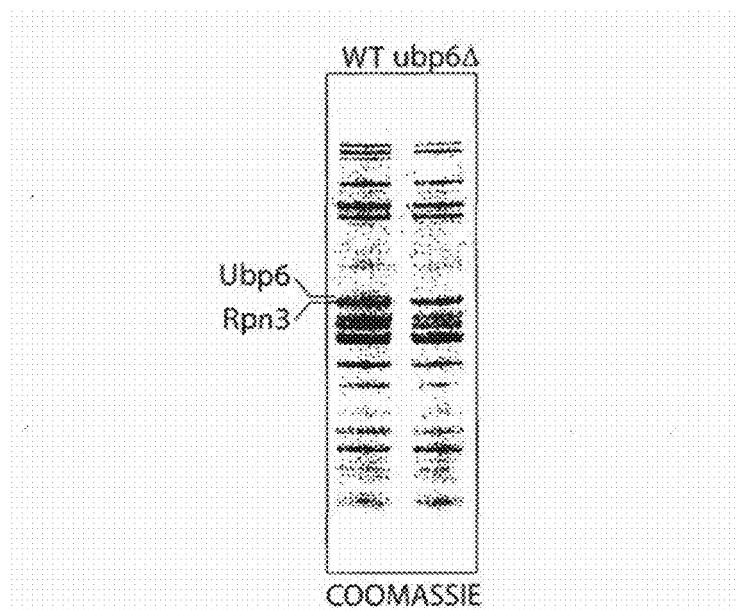
Figure 1E:
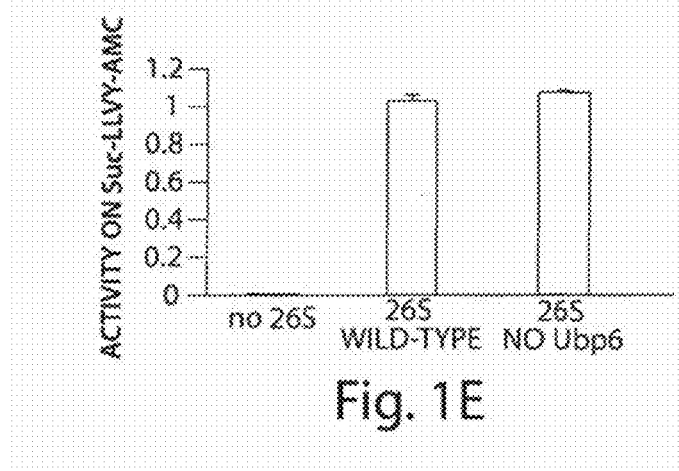
Figure 1F:
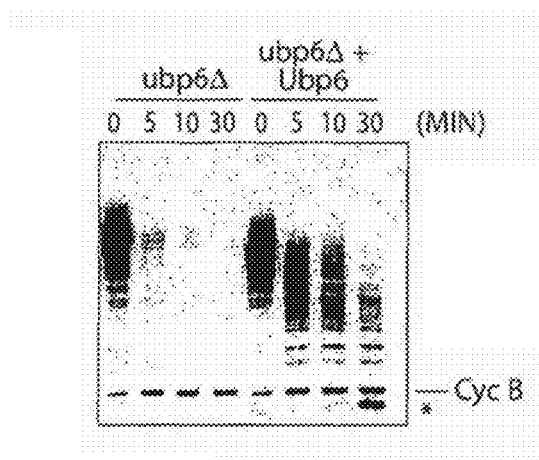
FIG. 1F depicts processing of ub-cyclin B by proteasomes in the presence of purified recombinant Ubp6 (* represents a cyclin B species generated by residual thrombin activity deriving from recombinant Ubp6 purifications).

To study the potential role of Ubp6 in proteasome function, an in vitro system for proteasome-mediated degradation of a model substrate was developed. Ubiquitination of the short-lived cell cycle regulator cyclin B was achieved via a reaction requiring E1, Ubc4 (E2), immunopurified APC (E3), ubiquitin, and ATP. Upon incubation of ubiquitinated cyclin B with proteasomes purified from ubp6Δ mutants, it was observed that the rate of cyclin B degradation was much greater than that of wild-type proteasomes (FIG. 1A). Significantly, the slower degradation of cyclin B exhibited by wild-type proteasomes was accompanied by progressive removal of ubiquitin groups from the substrate. The absence of Ubp6 in proteasomes purified from the ubp6Δ strain (FIG. 1B) was verified, and it was also verified that the amounts of proteasome were comparable between the two preparations (FIG. 1C).

The next studies were designed to determine whether the observed difference in cyclin B degradation was due specifically to Ubp6. Proteasomes were examined by Coomassie blue staining (FIG. 1D) and native gel electrophoresis, and no evidence for either an unexpected compositional difference or a gross structural abnormality in mutant proteasomes was found (see also Guterman and Glickman. (2004). Complementary roles for Rpn11 and Ubp6 in deubiquitination and proteolysis by the proteasome. J. Biol. Chem. 279, 1729-1738). Furthermore, the activity of mutant proteasomes against the peptide substrate suc-LLVY-AMC (SEQ ID NO: 1), which is hydrolyzed in an RP-dependent but ubiquitin-independent manner, was comparable to wild-type (FIG. 1E), indicating that inhibition of cyclin B degradation by Ubp6 was not due to suppression of the core proteolytic activity of the proteasome, nor to closing the gate into the CP. Comparable Ubp6 add-back results were obtained with ubp6Δ proteasomes purified using a CP affinity tag. Finally, when bacterially-expressed purified Ubp6 was added back to proteasomes lacking Ubp6, a marked inhibition of cyclin B degradation (FIG. 1F) was observed, indicating that Ubp6 itself is the inhibitory component of wild-type proteasomes. Inhibition of degradation by recombinant Ubp6 (FIG. 1F) was accompanied by progressive ubiquitin chain shortening, as seen with wild-type proteasomes (FIG. 1A).

Figure 1G:
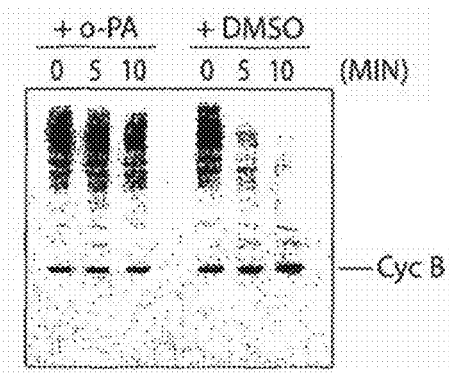
FIG. 1G depicts O-phenanthroline (o-PA) inhibition of cyclin B degradation by ubp6Δ proteasomes, implicating Rpn 11's deubiquitinating activity in this process. o-PA, dissolved in DMSO, was added at 10 mM, 10 min prior to cyclin B.

Rpn11 is known to promote deubiquitination and degradation by the proteasome (Verma, et al. (2002). Role of Rpn11 metalloprotease in deubiquitination and degradation by the 26S proteasome. Science 298, 611-615; Yao and Cohen. (2002). A cryptic protease couples deubiquitination and degradation by the proteasome. Nature 419, 403-407). To verify that Rpn11 was active in the system used herein, ubp6Δ proteasomes were used with the metal chelator o-phenanthroline (o-PA), an inhibitor of Rpn11. o-PA strongly inhibited deubiquitination and degradation of cyclin B (FIG. 1G). In contrast, o-PA treatment had no effect on LLVY-hydrolysis by proteasomes ('LLVY' disclosed as SEQ ID NO: 1). Thus, in contrast to Ubp6, Rpn11 promotes cyclin B degradation.

Example 3

In Vitro Confirmation of Proteasome Inhibition by Ubp6

Figure 2A:
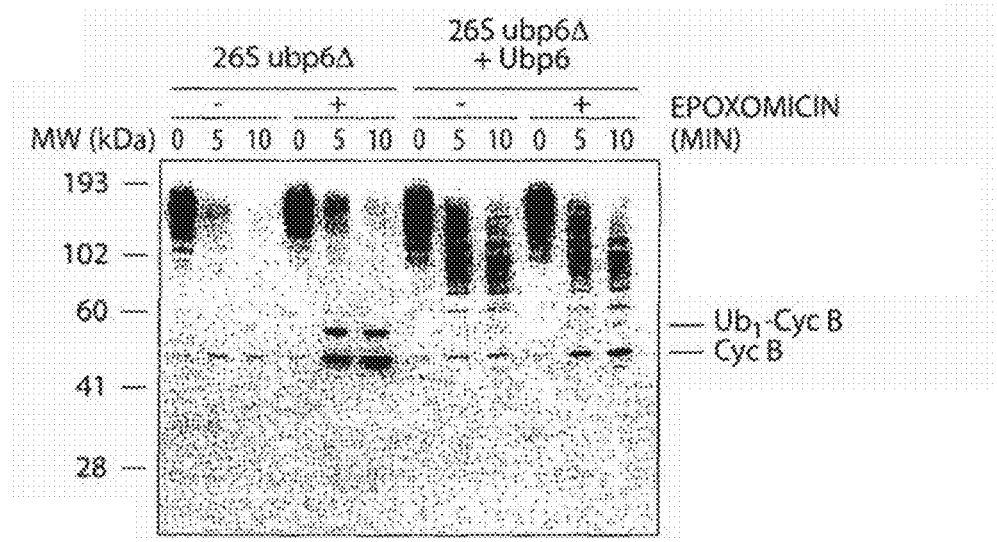
FIGS. 2A-2C are a series of illustrations depicting the inhibition of cyclin B degradation by epoxomicin.

Chemical inhibitors of the proteasome were used to confirm that the rapid disappearance of cyclin B in the absence of Ubp6 represents cyclin B degradation by proteasomes as opposed to a possible unknown component of the samples. For these experiments, epoxomicin, an inhibitor of the proteolytic active sites of the CP, was used. Epoxomicin preferentially targets the chymotrypsin-like activity of the CP; at high concentrations, such as used here, epoxomicin can inhibit all three proteolytic sites, although complete proteasome inhibition is generally not observed (Kisselev, et al. (2006) Importance of the proteasome's different proteolytic sites and the efficacy of inhibitors varies with the protein substrate. J. Biol. Chem. 281, 8582-90. Epub 2006 Feb. 2). The yield of deubiquitinated cyclin B reaction products from ubp6Δ proteasomes after a ten-minute incubation was greatly increased by epoxomicin, verifying that disappearance of cyclin B involved proteasome-mediated degradation (FIG. 2A). A diminished effect of epoxomicin was observed when the same experiment was carried out using proteasomes containing Ubp6, reflecting a reduced rate of cyclin B breakdown in the absence of epoxomicin (FIG. 2A). These Ubp6-dependent differences could be recapitulated by endogenous Ubp6 present in wild-type proteasomes (FIG. 2B).

The cyclin B used in the in vitro assay described herein may be linked through not only lys-48 (K48) of ubiquitin but also K11 and K63. K48 of ubiquitin was not required for in vitro degradation of ub-cyclin B. A side-by-side comparison of wild-type and ubp6Δ proteasomes; in both cases is provided herein, proteasomes deubiquitinate and degrade cyclin B without regard for the presence of K48 ubiquitin linkages in its attached ubiquitin chains (FIG. 2C). Thus, although K48-linked ubiquitin chains may be the dominant chain type promoting degradation in vivo, this linkage is not required for rapid proteasomal degradation in vitro. For many substrates, the requirement for K48 in protein degradation may reflect properties of the E3 enzymes involved in chain synthesis.

Figure 2B:
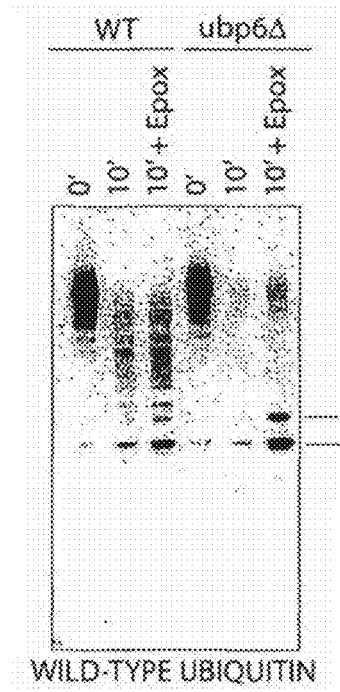
Figure 2C:
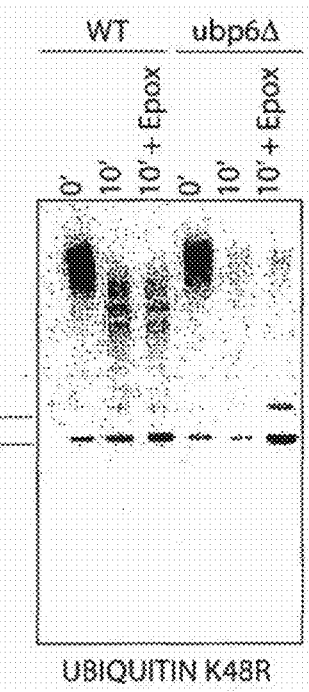

Finally, for reactions lacking Ubp6, epoxomicin stabilized, in addition to unmodified cyclin B, a second major species, which is apparently mono-ubiquitinated cyclin B (FIG. 2A-C). These results suggest that in the absence of Ubp6, while a majority of ubcyclin B is fully deubiquitinated by Rpn11 prior to degradation, a significant fraction is left incompletely deubiquitinated, and the resulting mono-ubiquitinated species is apparently rapidly degraded. In vivo, ubiquitin undergoes accelerated degradation by the proteasome in the absence of Ubp6 (Leggett, et al. (2002). Multiple associated proteins regulate proteasome structure and function. Mol. Cell. 10, 495-507; Hanna, et al. (2003). Ubiquitin depletion as a key mediator of toxicity by translational inhibitors. Mol. Cell. Biol. 23, 9251-9261; Chernova, et al. (2003). Pleiotropic effects of Ubp6 loss on drug sensitivities and yeast prion are due to depletion of the free ubiquitin pool. J. Biol. Chem. 278, 52102-52115; FIG. 5D). The assignment of mono-ubiquitinated cyclin B is consistent with previous studies. It was proposed that when Ubp6 is absent, one or more substrate-bound ubiquitin groups are translocated into the CP and degraded along with their substrate (see Leggett, et al. (2002). Multiple associated proteins regulate proteasome structure and function. Mol. Cell. 10, 495-507), but until now there had been no biochemical basis to account for accelerated ubiquitin turnover. It was proposed that increased turnover of mono-ubiquitinated degradative intermediates as suggested by FIG. 2 may contribute significantly to the rapid degradation of ubiquitin in vivo in the absence of Ubp6.

Example 4

Ubp6 Impairs Proteasome-Mediated Degradation In Vivo

The in vitro data predicted accelerated degradation of at least some proteasomal substrates in vivo in the absence of Ubp6. To test this idea, chromosomal integration was used to render the biosynthetic enzymes Trp1 and Ura3 unstable by appending an N-terminal segment that directs these proteins to the N-end rule pathway for degradation (Varshaysky. (2005). Regulated protein degradation. Trends Biochem. Sci. 30, 283-286). Accordingly, growth of such strains in the absence of the relevant metabolite should reflect the rate of degradation of the respective reporter protein. Strains harboring proteolytic defects should stabilize the reporters, and thus display increased growth relative to wild-type. Ubr1, the E3 of the N-end rule pathway, governs ubiquitination of the reporter proteins. As expected, the ubr1Δ mutant displayed a strong growth advantage over wild-type when cultured on media lacking tryptophan (FIG. 3A) or uracil.

Although such assays have typically been used to characterize degradation defects, it was reasoned that if significant growth were detectable in wild-type strains, the assay could also be used to identify mutants with increased degradation rates. Indeed, when ubp6Δ mutants were tested, they displayed a dramatic growth defect relative to wild-type (FIG. 3A), consistent with a proteasome hypermorphic effect. Additionally, a ubr1Δ ubp6Δ double mutant retained the robust growth phenotype of the ubr1Δ single mutant, ruling out a protein synthesis defect as the cause of the poor growth of the ubp6Δ strain. Ura3 reporter strains that are wild-type for UBP6 showed no growth in the absence of uracil, precluding the corresponding comparison.

Figure 3A:
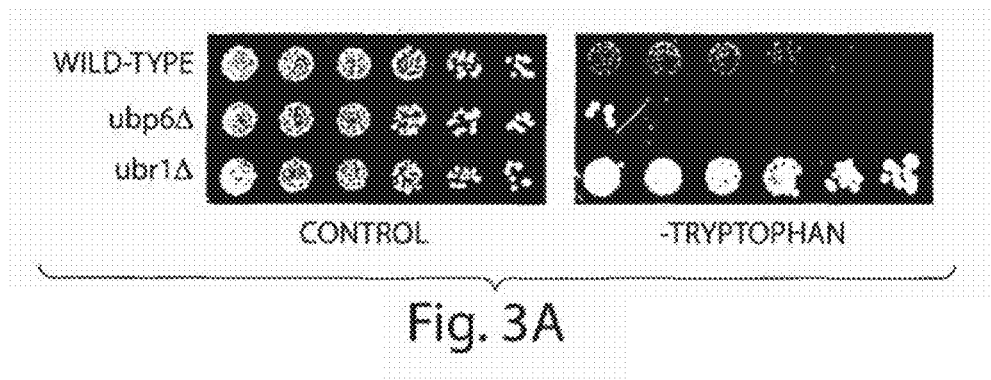
FIGS. 3A and 3B are a series of illustrations depicting that deletion of the UBP6 gene accelerates degradation of a proteasome substrate in vivo.
Figure 3B:
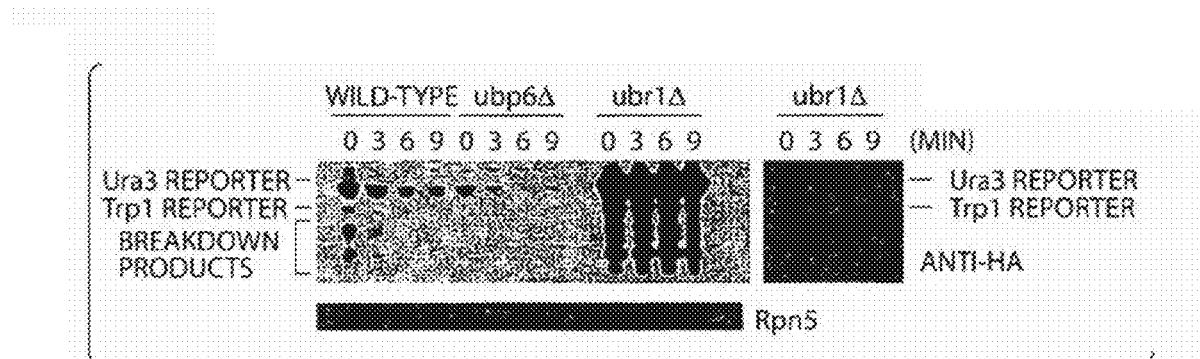

The results from FIG. 3A suggested that the reporter proteins were turned over more rapidly in the ubp6Δ strain. To test this idea directly, cycloheximidechase analyses were conducted in strains harboring both reporter constructs. In the wild-type strain rapid degradation of both reporters was observed, with half-lives on the order of several minutes (FIG. 3B). In the ubr1Δ mutant, both reporters were highly stabilized (FIG. 3B). In contrast, in the ubp6Δ mutant, the Ura3 reporter disappeared more rapidly than in wild-type, and showed a decreased steady-state level (FIG. 3B). Steady-state levels of the Trp1 reporter were also depressed in the ubp6Δ mutant (FIG. 3B), falling below the level of detection. The level of a control protein, proteasome subunit Rpn5, remained constant throughout, indicating the specificity of these effects.

Figure 7:
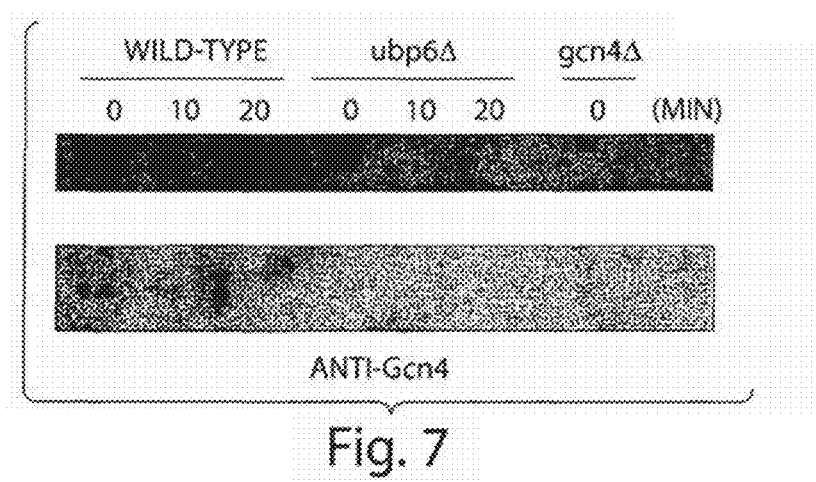
FIG. 7 is an illustration depicting cycloheximide-chase analysis of Gcn4 turnover in wild-type and ubp6Δ strains. Logarithmically growing cells were treated with cycloheximide (20 μg/ml) and aliquots were taken at the indicated times. Cells were immediately resuspended in 1× Laemmli loading buffer, and endogenous Gcn4 was detected by immunoblot using anti-Gcn4 antibody. The bottom panel is a lower exposure of the blot above.

In addition to N-end Rule substrates, the short-lived transcription factor Gcn4, expressed from its own promoter in untagged form, was evaluated. Again, accelerated degradation in the ubp6Δ mutant was observed, with a concomitant decrease in steady-state levels (FIG. 7). Thus, multiple short-lived proteins are turned over more rapidly in vivo in the absence of Ubp6.

Example 5

The Deubiquitinating Activity of Ubp6 is not Required for Proteasome Inhibition

Figure 4A:
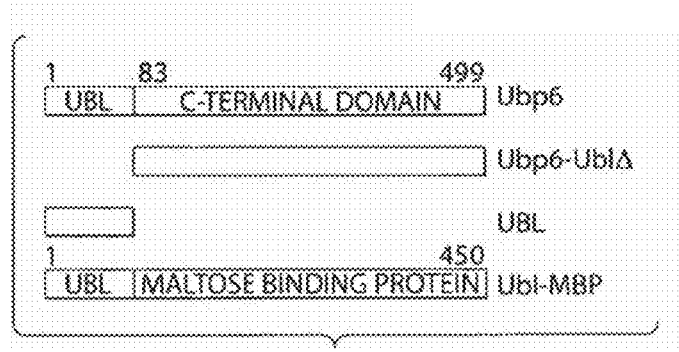

To determine which functional elements of Ubp6 are required for inhibiting proteasome function, a number of Ubp6 mutants were generated and tested (FIG. 4A). An N-terminal ubiquitin-like domain (Ubl) is necessary and sufficient to mediate binding to the proteasome, but is not required for the catalytic activity of purified Ubp6 (Leggett, et al. (2002). Multiple associated proteins regulate proteasome structure and function. Mol. Cell. 10, 495-507). Deletion of the Ubl domain rendered Ubp6 non-inhibitory in the cyclin B degradation assay (FIG. 4B), suggesting that Ubp6 must be bound to the proteasome to inhibit cyclin B degradation. The Ubl domain by itself also had no effect on cyclin B degradation (FIG. 4E). Thus, the ability of Ubp6 to inhibit degradation of cyclin B jointly requires the Ubl and C-terminal domains of the protein.

Figure 4B:
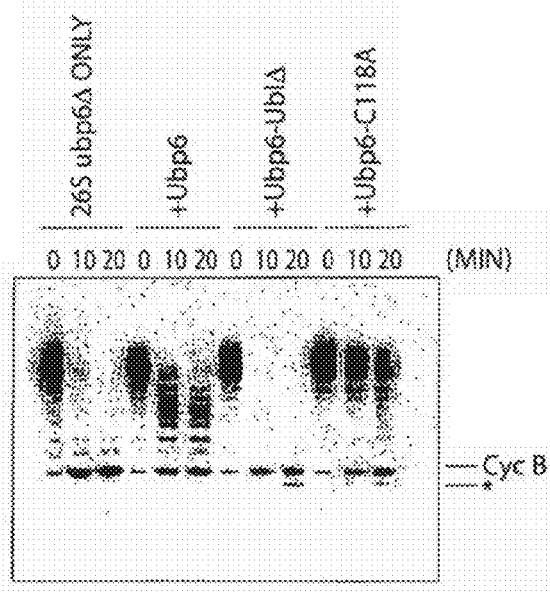
Figure 8:
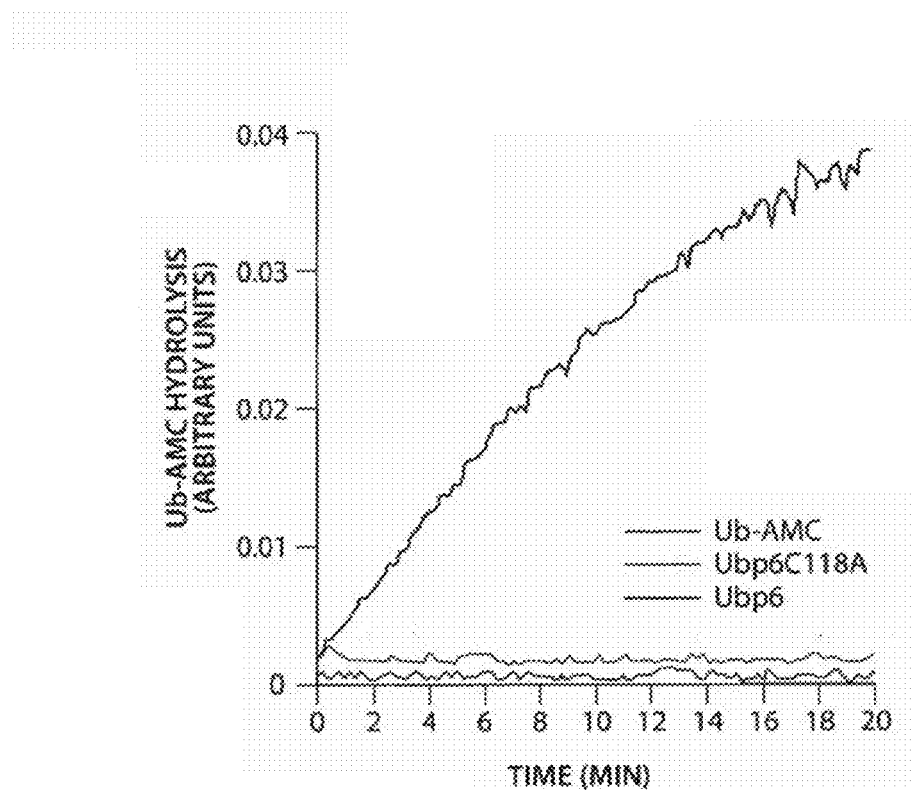
FIG. 8 is a graph depicting that the Ubp6-C118A mutant lacks deubiquitinating activity. Ub-AMC hydrolyzing activity of purified recombinant wild-type Ubp6 or Ubp6-C118A (0.5 μM). Ub-AMC, no enzyme control.

Although efficient degradation of ubiquitin conjugates by the proteasome is thought to require removal of ubiquitin groups prior to translocation of the substrate into the CP, premature removal of ubiquitin chains could result in dissociation of the substrate and antagonize its degradation (Lam, et al. (1997). Editing of ubiquitin conjugates by an isopeptidase in the 26S proteasome. Nature 385, 737-740). Such a scenario could provide a straightforward means by which deubiquitinating activity at the proteasome could inhibit protein breakdown. The joint requirements of the Ubl and C-terminal domains of Ubp6 for inhibiting cyclin B degradation are consistent with this view. However, a catalytically inactive point mutant of Ubp6 (Ubp6-C118A) proved competent for inhibition (FIG. 4B). Inhibition of degradation by Ubp6-C118A was also observed using proteasomes purified via a CP affinity tag. Thus, Ubp6 does not prevent cyclin B degradation simply through premature deubiquitination. To substantiate this conclusion, it was verified that Ubp6-C118A is completely devoid of deubiquitinating activity against the model substrate Ub-AMC (FIG. 8), but retains wild-type binding affinities for the proteasome (Chernova, et al. (2003). Pleiotropic effects of Ubp6loss on drug sensitivities and yeast prion are due to depletion of the free ubiquitin pool. J. Biol. Chem. 278, 52102-52115; Leggett, et al. (2002). Multiple associated proteins regulate proteasome structure and function. Mol. Cell. 10, 495-507).

Figure 9A:
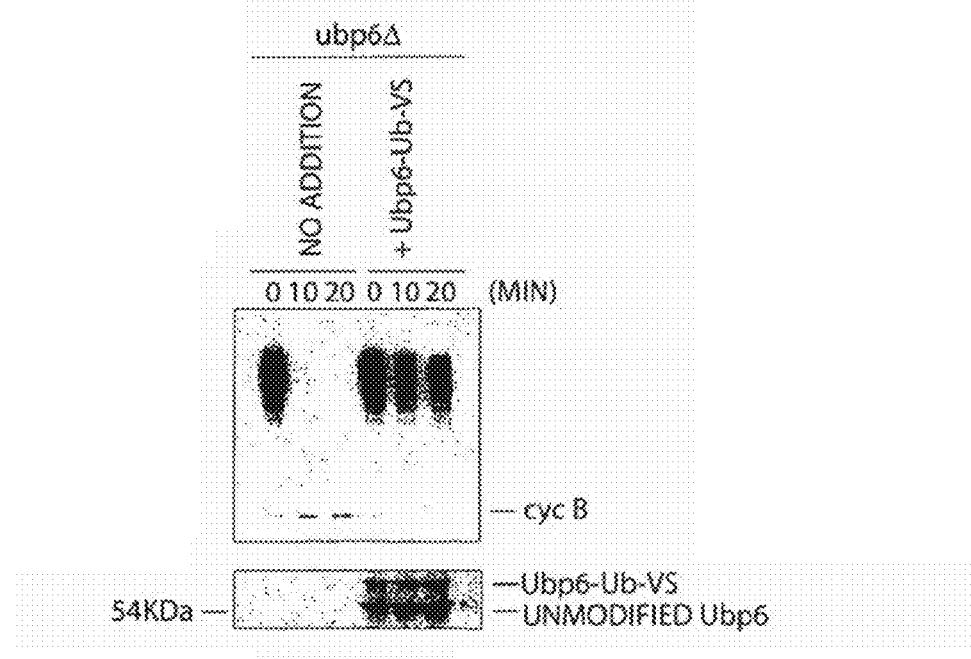
FIGS. 9A and 9B are a series of illustrations and a graph depicting that ubiquitin-vinyl sulfone treated Ubp6 retains non-catalytic inhibition of degradation.
Figure 9B:
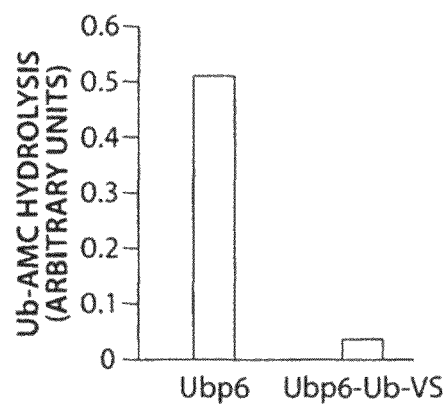

As an alternate approach to assay non-catalytic inhibition, ubiquitin-vinyl sulfone (Ub-VS), an irreversible active site inhibitor of Ubp6, was used. Residual Ub-AMC hyrdolyzing activity in the presence of Ubp6-Ub-VS is at the level of background in this assay. Although it completely eliminated catalytic activity of wild-type Ubp6 as measured by Ub-AMC hydrolysis, inhibition of cyclin B degradation by Ubp6 persisted (FIG. 9). This finding also indicates that inhibition of degradation by Ubp6-C118A cannot be attributed to nonproductive ubiquitin chain binding at the active site of the mutant enzyme. Indeed the large excess of substrate over Ubp6 (see Methods described in Example 1) is inconsistent with a model in which Ubp6 inhibits degradation by sequestering substrate. Taken together, these data show that Ubp6 has two distinct functions, one catalytic and one non-catalytic. Although these functions are distinct, each requires both the Ubl domain and the C-terminal domain. The Ubl domain serves in both cases to target Ubp6 to the proteasome, and that both functions are obligatorily executed on the proteasome.

Although Ubp6-C118A was, like wild-type Ubp6, competent to inhibit cyclin B degradation, the fate of cyclin B over the time course of the incubation was affected by the loss of deubiquitinating activity in the mutant enzyme. When wild-type Ubp6 was used for reconstitution, a progressive reduction in electrophoretic mobility of cyclin B immunoreactive material was seen, whereas these mobility shifts were not observed with Ubp6-C118A (FIG. 4B). These data imply that the mobility shifts represent trimming of ubiquitin or ubiquitin chains bound to cyclin B, and that the trimming reaction is mediated predominantly or exclusively by the deubiquitinating activity of Ubp6.

To quantify the extent of proteasome inhibition by Ubp6, a method of quantitative mass spectrometry was utilized. After a 20-minute incubation, approximately half of the total cyclin B was degraded by ubp6Δ proteasomes (FIG. 4C). High molecular weight ubiquitin-cyclin B conjugates were almost completely eliminated by this time, but degradation would not be expected to go to completion because a fraction of the input cyclin B had not been ubiquitinated. Addition of purified Ubp6 or Ubp6-C118A resulted in approximately 70% inhibition of degradation at this time point (FIG. 4C), which may underestimate the Ubp6 inhibitory effect, since the course of degradation seemed to be nearing completion in the control sample.

Example 6

Ubp6 Prevents Rpn11-Dependent Ubiquitin Chain Removal

The linkage of Rpn11 activity to substrate degradation can be abrogated by proteasome inhibitors, presumably because they act downstream of Rpn11 (Verma, et al. (2002). Role of Rpn11 metalloprotease in deubiquitination and degradation by the 26S proteasome. Science 298, 611-615; Yao and Cohen. (2002). A cryptic protease couples deubiquitination and degradation by the proteasome. Nature 419, 403-407). Thus, to visualize the activity of Rpn11 on cyclin B, proteasome inhibitor treated ubp6Δ proteasomes were used, as in FIG. 2. This figure showed, as described above, that the effect of Ubp6 on cyclin B disappearance is mediated by an altered rate of proteasome-mediated degradation. However, since the results of FIG. 4 indicate that the deubiquitination seen during degradation delay is mediated by Ubp6, and not by Rpn11, Ubp6 inhibits the proteasome at a point in the reaction pathway such that Rpn11-mediated chain removal is prevented.

In the presence of epoxomicin, Rpn11 can be seen to cleave substrate-linked chains at or near their base, resulting in the production of a prominent band of unmodified substrate protein (Verma et al., 2002; Yao et al., 2002; FIG. 2). When the reaction products from wild-type and ubp6Δ proteasomes pre-treated with epoxomicin were compared, a greater amount of unmodified cyclin B was observed in ubp6Δ reactions, reflecting substrate deubiquitinated but not degraded by the proteasome (FIG. 2A-C). In the presence of Ubp6, a lesser amount of unmodified cyclin B was stabilized by the inhibitor; instead, the majority of the cyclin B remained as higher molecular weight species, most likely reflecting partial deubiquitination. The increased yield of unmodified cyclin B in the presence of ubp6Δ proteasomes as compared to wild-type indicates that Rpn11-dependent chain removal from substrate is suppressed in the presence of Ubp6. However, it remains unclear whether Ubp6 directly inhibits Rpn 11 or some other activity that may function upstream of Rpn11.

Example 7

Interference with Substrate-Proteasome Interaction Cannot Explain Proteasome Inhibition by Ubp6

One explanation for the degradation-inhibitory effect of Ubp6 is that binding of Ubp6 to the proteasome is competitive with that of substrate. Several lines of evidence indicate that Ubp6 does not inhibit the proteasome by this mechanism. As seen in FIG. 4B, the deubiquitination of cyclin B that occurs in the complete reaction mixture is mediated by Ubp6. However, when Ubp6 is incubated in the presence of cyclin B, but without proteasomes, no deubiquitination of cyclin B is observed (FIG. 4D). Thus, Ubp6 requires the proteasome for its deubiquitinating activity on cyclin B. These data suggest that both Ubp6 and cyclin B are bound to proteasomes so long as cyclin B deubiquitination proceeds, which can be an extended period, since the deubiquitination reaction is progressive over the time courses shown in FIG. 4.

Figure 10A:
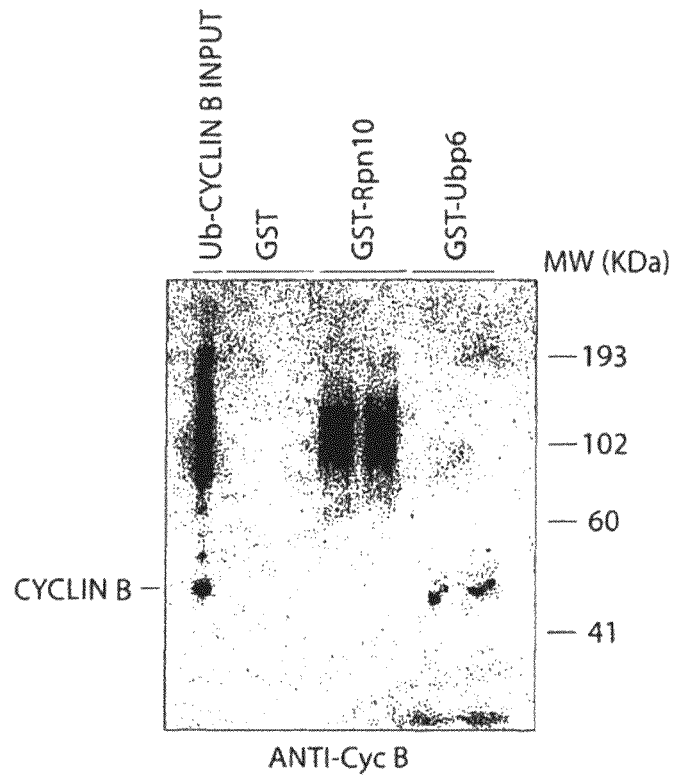
FIGS. 10A and 10B are illustrations depicting the results of the Ub-Cyclin B binding assay. Resins bearing GST, GST-Rpn 10, and GST-Ubp6 were incubated with Ub-cyclin B. Excess glutathione was used to elute complexes, and eluates (10% of total) were visualized by immunoblot with anti-Cyclin B antibody (FIG. 10A) or Coomassie staining (FIG. 10B). No detectable binding of Ub-Cyclin B conjugates was observed with GST-Ubp6. Rpn 10, a known ubiquitin receptor, served as a positive control. Input lane represents 2.5% of the total Ub-cyclin B per reaction.
Figure 10B:
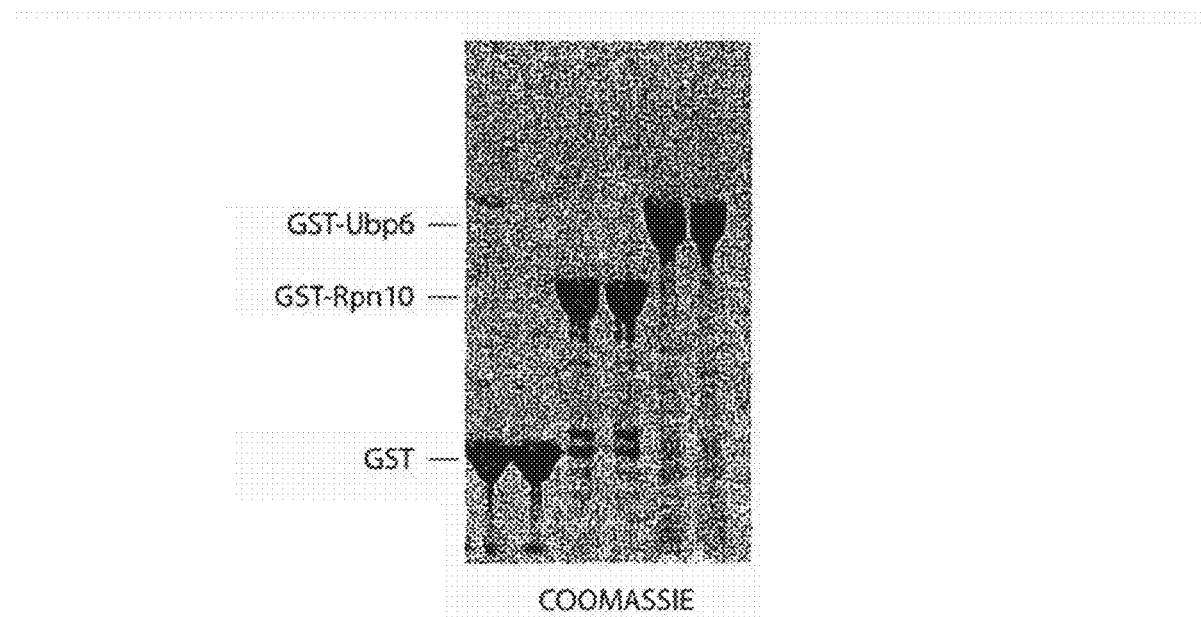

Ubp6 could conceivably inhibit cyclin B degradation via a substrate-titration mechanism. However, direct interaction between Ubp6 and ub-cyclin B were not able to be observed using a GST pull down assay that sensitively detects binding of ub-cyclin B to ubiquitin receptors such as Rpn10, Rad23, and Dsk2 (FIG. 10). These findings are consistent with a previous report that the KM of Ubp6 for ubiquitin ethyl ester is so high as to be unmeasurable (Chernova, et al. (2003). Pleiotropic effects of Ubp6 loss on drug sensitivities and yeast prion are due to depletion of the free ubiquitin pool. J. Biol. Chem. 278, 52102-52115).

Ubp6 is large enough, at 57 kDa, that its presence on the proteasome could conceivably impede binding of substrates or substrate receptors. Also, the pathway of substrate translocation through the proteasome might be blocked by non-specific steric interference. To address this possibility a fusion protein in which the Ubl of Ubp6 was fused N-terminally to the maltose binding protein of *E. coli* was constructed (FIG. 4A), resulting in a fusion protein of nearly the same size as Ubp6. Despite binding the proteasome, this construct, as for the Ubl alone, failed to inhibit cyclin B degradation (FIG. 4E).

Figure 4F:
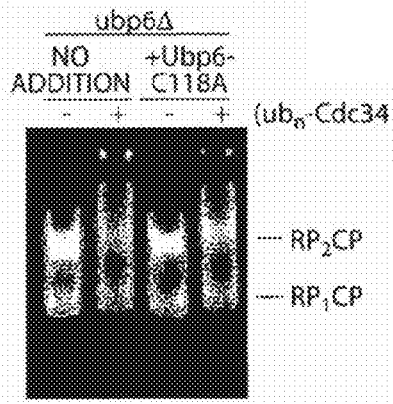

Finally, the effect of Ubp6 on conjugate binding to the proteasome by using auto-ubiquitinated Cdc34, a substrate that binds proteasomes but is not degraded, was directly evaluated (Elsasser, et al. (2004). Rad23 and Rpn10 serve as alternative ubiquitin receptors for the proteasome. J. Biol. Chem. 279, 26817-26822). Using an activity-based electrophoretic mobility shift assay (Elsasser et al., 2004), comparable conjugate binding was observed in the presence and absence of Ubp6-C118A (FIG. 4F). Conjugate binding was observed in the presence of wild-type Ubp6, but was also accompanied by deubiquitination, as determined by immunoblot. Taken together, the data of FIGS. 4E and 4F indicate that non-catalytic proteasome inhibition by Ubp6 is unlikely to be achieved through simple sterically-based mechanisms, but instead may involve specific functionalities within the C-terminal domain of Ubp6.

Example 8

In Vivo Differentiation of ubp6Δ and ubp6-C118A Mutants

Figure 5B:
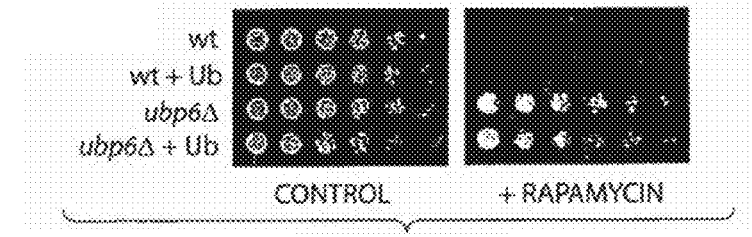
Figure 5C:
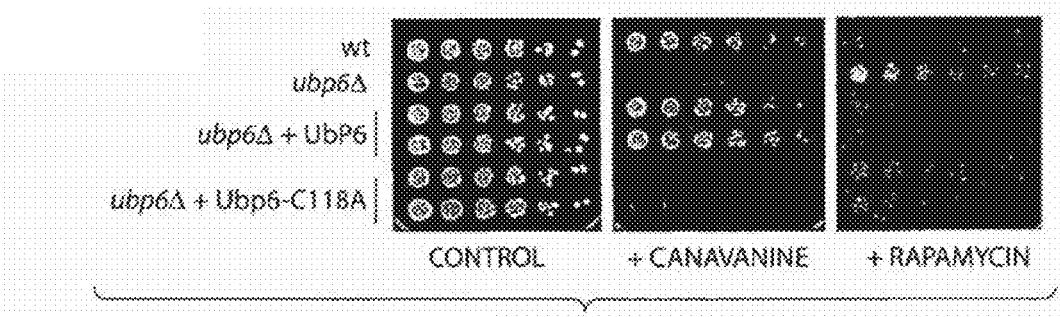
Figure 11:
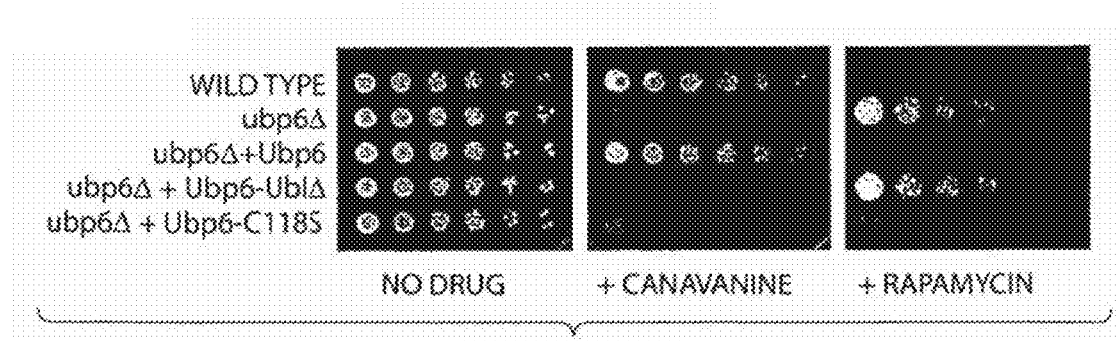
FIG. 11 is an illustration depicting that the rapamycin-related functions of Ubp6 require its ubiquitin-like domain. Wild-type (SUB62) and ubp6Δ (SY255c) strains were transformed with empty vector (WTD72) or plasmids encoding Ubp6 (WTD72), Ubp6-ublΔ (WTD73), or Ubp6-C118S (WTD74) expressed from the GAP1 promoter. Cultures were spotted in three-fold serial dilutions onto selective plates containing canavanine (1.5 mg/ml) or rapamycin (200 ng/ml), and grown for 2-7 days at 30° C.

The next studies were designed to generate in vivo evidence for the nonequivalence of the null and catalytic point mutants of Ubp6. A number of ubp6Δ phenotypes that can be suppressed by ubiquitin overexpression have been described (Chernova et al., 2003; Hanna, et al. (2003). Ubiquitin depletion as a key mediator of toxicity by translational inhibitors. Mol. Cell. Biol. 23, 9251-9261), including hypersensitivity to the amino acid analog canavanine (FIG. 5A) and to several translational inhibitors. Intriguingly, it was found that not all ubp6Δ phenotypes are ubiquitin dependent. For instance, a strong resistance of ubp6Δ to rapamycin was observed, which was not suppressed by ubiquitin overexpression (FIG. 5B). This result suggests functions of Ubp6 outside of ubiquitin regeneration, possibly reflecting noncatalytic functions of Ubp6. To test this hypothesis, wild-type Ubp6 and Ubp6-C118A from its endogenous promoter were expressed in a ubp6Δ strain. Wild-type Ubp6 complemented both the canavanine and rapamycin phenotypes (FIG. 5C). As expected, expression of Ubp6-C118A failed to rescue canavanine hypersensitivity (FIG. 5C; Leggett, et al. (2002). Multiple associated proteins regulate proteasome structure and function. Mol. Cell. 10, 495-507), but in contrast largely complemented rapamycin resistance (FIG. 5C). Ubp6-ub1A recapitulated the null phenotype, suggesting that the rapamycin-related non-catalytic functions of Ubp6 occur on the proteasome (FIG. 11). These results provide in vivo evidence that the ubp6Δ and ubp6-C118A mutants are not equivalent, and support the hypothesis that Ubp6 performs non-catalytic functions, as observed in vitro.

In the absence of Ubp6, free ubiquitin is rapidly turned over (FIG. 5D; Leggett et al., 2002). The failure of Ubp6-C118A to complement ubiquitin-dependent phenotypes such as canavanine hypersensitivity suggested aberrant ubiquitin turnover in ubp6-C118A mutants. Overexpression of wild-type Ubp6, but not Ubp6-C118A, restored ubiquitin stability (FIG. 5D), indicating that the ubiquitin recycling function of Ubp6 is catalytic in nature. These results provided a mechanistic basis for understanding why the Ubp6-C118A mutation affects ubiquitin-dependent but not ubiquitin-independent phenotypes, and indicated that the non-catalytic function of Ubp6 is distinct from its function in ubiquitin homeostasis.

Finally, the Ub-K-Trp 1 substrate described in FIG. 3 was used to test whether non-catalytic inhibition of degradation by Ubp6 was also operational in vivo. As shown in FIG. 5E, expression of Ubp6-C118A restored growth on media lacking tryptophan, indicating stabilization of the Ub-K-Trp1 protein. Importantly, wild-type Ubp6 was more effective in stabilizing Ub-K-Trp1 than was Ubp6-C118A. Thus both catalytic and non-catalytic features of Ubp6 mediate proteasome inhibition in vivo.

Example 9

Regulatory Particle is Sufficient for Deubiquitination by Ubp6 but not Rpn11

Rpn11 has been reported to function in the context of the 26S proteasome, but not in the context of the RP or the lid (Verma, et al. (2002). Role of Rpn11 metalloprotease in deubiquitination and degradation by the 26S proteasome. Science 298, 611-615), although there have been differing reports (Yao and Cohen. (2002). A cryptic protease couples deubiquitination and degradation by the proteasome. Nature 419, 403-407; Guterman and Glickman. (2004). Complementary roles for Rpn11 and Ubp6 in deubiquitination and proteolysis by the proteasome. J. Biol. Chem. 279, 1729-1738). In the assay used herein, RP purified from a ubp6Δ mutant produced no detectable deubiquitination of cyclin B conjugates (FIG. 6A). In contrast, addition of purified Ubp6 to RP resulted in chain shortening, although to a lesser extent than with 26S proteasomes (FIG. 6A). Addition of Ubp6-C118A to RP had no effect on substrate processing (FIG. 12), further verifying that ubiquitin chain shortening seen with wild-type Ubp6 reflects the catalytic activity of Ubp6 itself. The cyclin B immunoreactivity before and after Ubp6 processing was of approximately equal intensity, consistent with the view that Ubp6 shortens ubiquitin chains, but rarely produces unmodified substrate as does Rpn11.

Figure 12:
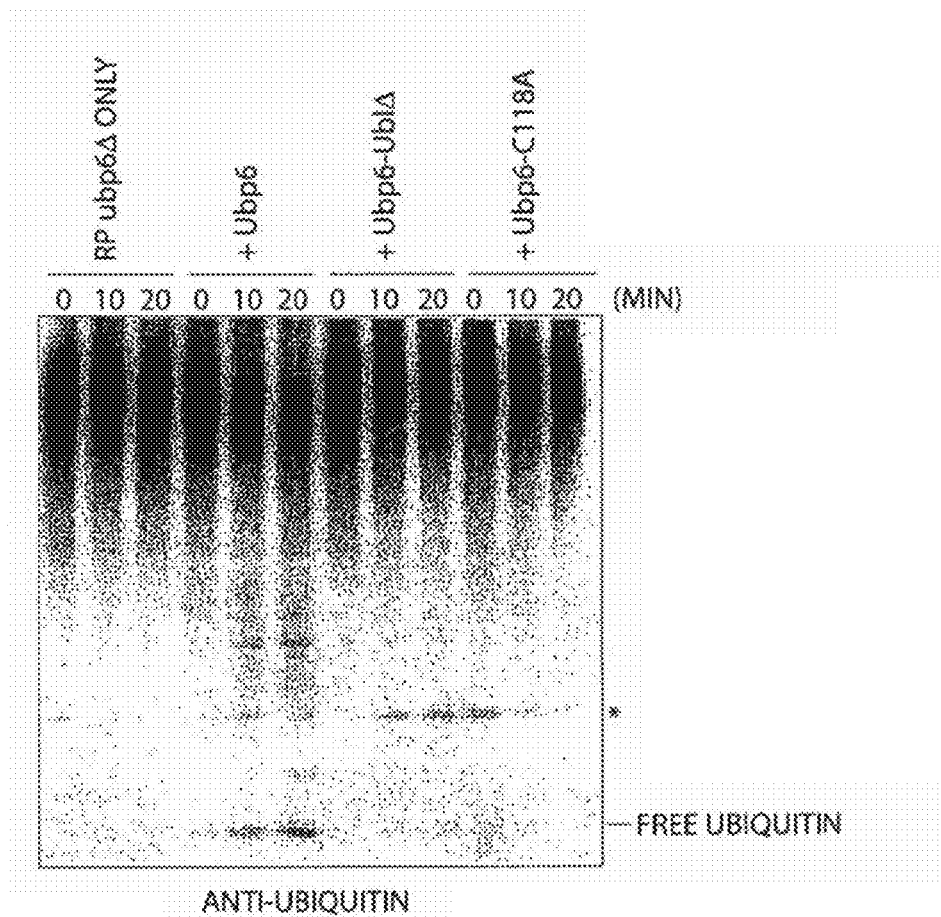
FIG. 12 is an illustration depicting the RP-mediated disassembly of Ub-cyclin B conjugates by Ubp6. Proteasome regulatory particle (135 nM) purified from a ubp6Δ strain was combined with a four-fold molar excess of Ubp6, Ubp6-ublΔ, or Ubp6-C118A, and Ub-Cyclin B, and incubated for the indicated times. Reactions were visualized by immunoblot with anti-ubiquitin antibody. *represents a non-ubiquitin immunoreactive band.
Figure 13:
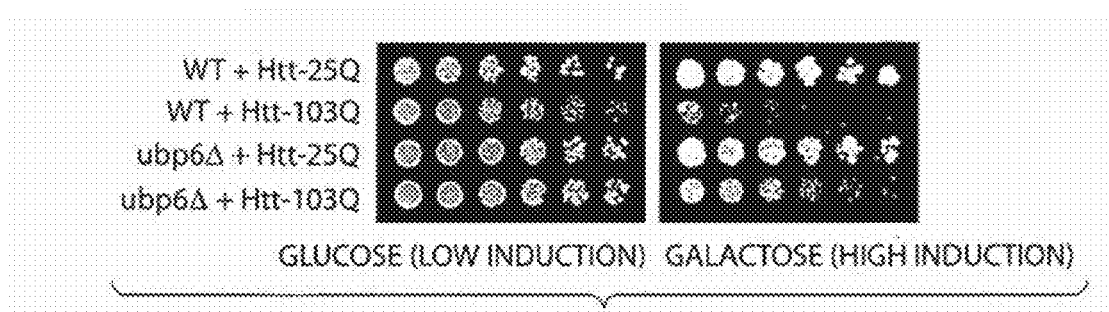
FIG. 13 is an illustration depicting that loss of Ubp6 function protects cells against Huntington-mediated toxicity. Wild-type and ubp6Δ cells were transformed with plasmids encoding non-pathogenic and pathogenic versions of the Huntington protein, expressed from a GAL promoter. Cells were spotted in 3-fold serial dilutions on media containing glucose (weak expression of Htt genes) or galactose (strong expression of Htt genes).

The fate of ubiquitin in the presence of RP-bound Ubp6 was examined by anti-ubiquitin immunoblots. A decrease in the overall size and intensity of the high molecular weight material was found, consistent with the data from FIG. 6A, but reaction products were also observed co-migrating with di-ubiquitin, tri-ubiquitin, and larger ubiquitin polymers (FIG. 6B). Presumably, mono-ubiquitin was also generated, although this was difficult to discern because of the high levels of free ubiquitin present in the reactions. In reactions utilizing lower amounts of substrate, Ubp6-dependent generation of free ubiquitin was readily observed (FIG. 12). These results suggest a preference of Ubp6 for the distal end of ubiquitin chains (see also Hu, et al. (2005). Structure and mechanisms of the proteasome-associated deubiquitinating enzyme USP14. EMBO J. 24, 3747-3756); alternately, Ubp6 may cleave proximally to remove mono-ubiquitin and small ubiquitin chains. A third deubiquitinating enzyme, Uch37, which is absent from budding yeast, has been reported to possess a distal-end-directed activity on the proteasome (Lam, et al. (1997). Editing of ubiquitin conjugates by an isopeptidase in the 26S proteasome. Nature 385, 737-740). However, whereas Uch37 appears to remove ubiquitins one at a time, shortening of chains by Ubp6 is not limited to the trimming of single ubiquitins.

Example 10

The In Vitro Functions of Ubp6 are Evolutionarily Conserved

Ubp6 and its human homolog Usp14 share 32% sequence identity (Chernova, et al. (2003). Pleiotropic effects of Ubp6loss on drug sensitivities and yeast prion are due to depletion of the free ubiquitin pool. J. Biol. Chem. 278, 52102-52115). Several features of Ubp6, including proteasome binding and activation by proteasome binding, are shared by Usp14 (Borodovsky, et al. (2001). A novel active site-directed probe specific for deubiquitylating enzymes reveals proteasome association of USP14. EMBO J. 20, 5187-5196). Indeed, overexpressed Usp14 complements several in vivo phenotypes of ubp6Δ in yeast (Chernova et al., 2003). It was therefore tested whether purified recombinant Usp14 could substitute for Ubp6 in the cyclin B degradation assay, using ubp6Δ proteasomes from yeast. Usp14 largely recapitulated the effects of Ubp6 (FIG. 6C): ub-cyclin B was not only stabilized against degradation by Usp14, but progressively deubiquitinated to lower molecular weight forms. Usp14 is slightly less efficient than Ubp6 in this assay, perhaps reflecting a decreased affinity of Usp14 for yeast proteasomes compared to Ubp6. These results, in combination with the reported in vivo complementation of ubp6Δ by Usp14, indicate that the observed effects of Ubp6 in this reconstituted system are likely to represent major functions of Ubp6 in vivo.

Example 11

Inhibition of Human Proteasome by Usp14: Dominant Catalytic Component

Figure 14:
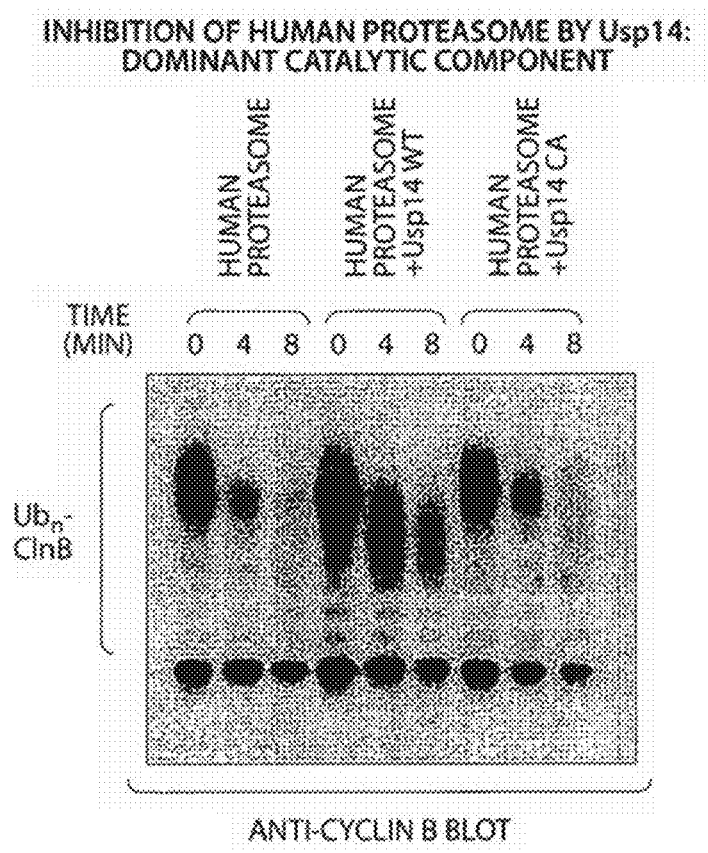
FIG. 14 is an illustration depicting the inhibition of proteasome by Usp14.

In the study shown in FIG. 14, 4 nM of human proteasomes were incubated with approximately 30 nM of ubiquitinated cyclin B in buffer (50 mM Tris [pH 7.5], 5 mM $MgCl_2$, and 5 mM ATP). Where indicated, 15-fold molar access of Usp14 over proteasome (60 nM) was preincubated for 5 min before initiating degradation reactions. Ubiquitinated cyclin B was added at time zero. SDS-sample buffer was added to stop the reaction at the indicated time. Usp14 CA is a variant of Usp14 with a single amino acid substitution that eliminates the active site nucleophile of the enzyme (a cysteine to alanine replacement). Usp14 WT is the wild-type or unmutated, catalytically active form of the enzyme. In the three lanes at left, no Usp14 was added. The data show that the ability of Usp14 to remove ubiquitin chains from the substrate is critical to its suppression of cyclin B degradation, which applies to other proteasome substrates. These findings indicate that small-molecule inhibitors of the catalytic activity of Usp14 accelerate proteasome action on ubiquitinated substrates.

The invention having now been described by way of written description and example, those of skill in the art will recognize that the invention can be practiced in a variety of embodiments and that the description and examples above are for purposes of illustration and not limitation of the following claims.

What is claimed is:

1. A method of screening for a Usp14 inhibitor comprising:
   (a) forming a Usp14 polypeptide/proteasome complex under conditions sufficient to form said complex;
   (b) contacting said Usp14 polypeptide/proteasome complex with a test compound; and
   (c) determining whether said test compound dissociates the Usp14 polypeptide/proteasome complex,
   whereby dissociation of the Usp14 polypeptide/proteasome complex indicates that said test compound is a Usp14 inhibitor.

2. The method of claim 1, wherein said test compound is a small molecule.

3. The method of claim 1, wherein said proteasome is selected from the group consisting of a yeast proteasome, a murine proteasome and a human proteasome.

4. The method of claim 1, wherein said test compound is detectably labeled.

5. A method comprising:
   (a) providing a test solution comprising Usp14 polypeptide;
   (b) contacting said test solution with a test compound and a substrate of said Usp14 polypeptide, wherein said substrate is coupled to a reporter that is detectable after cleavage by a deubiquitinating enzyme;
   (c) determining whether said substrate is deubiquitinated in the presence of the test compound and the Usp14 polypeptide,
   whereby a decrease in deubiquitination of the substrate in the presence of the test compound and the Usp14 polypeptide indicates that said test compound is an inhibitor of Usp14.

6. The method of claim 5, wherein said substrate is ubiquitin-AMC.

7. The method of claim 5, wherein said test compound is a small molecule.

8. The method of claim 5, wherein said reporter is fluorescently labeled.

9. The method of claim 5, comprising the steps:
   (a)' providing a test solution comprising Usp14 polypeptide and a proteasome under conditions sufficient to allow the Usp14 polypeptide and proteasome to form a complex;
   (b)' contacting said test solution with a test compound and a substrate of said Usp14 polypeptide/proteasome, wherein said substrate is coupled to a reporter that is detectable after cleavage by a deubiquitinating enzyme;
   (c)' determining whether said substrate is deubiquitinated in the presence of the test compound and the Usp14 polypeptide/proteasome complex,
   whereby a decrease in deubiquitination of the substrate in the presence of the test compound and the Usp14 polypeptide/proteasome complex indicates that said test compound is an inhibitor of Usp14.

\* \* \* \* \*